United States Patent
Gray et al.

(10) Patent No.: US 12,275,948 B2
(45) Date of Patent: Apr. 15, 2025

(54) OPTIMIZED CLN5 GENES AND EXPRESSION CASSETTES AND THEIR USE

(71) Applicants: THE UNIVERSITY OF NORTH CAROLINA AT CHAPEL HILL, Chapel Hill, NC (US); LINCOLN UNIVERSITY, Lincoln (NZ)

(72) Inventors: Steven James Gray, Southlake, TX (US); David Palmer, Christchurch (NZ); Nadia Mitchell, Christchurch (NZ)

(73) Assignees: The University of North Carolina at Chapel Hill, Chapel Hill, NC (US); Lincoln University, Lincoln (NZ)

( * ) Notice: Subject to any disclaimer, the term of this patent is extended or adjusted under 35 U.S.C. 154(b) by 1027 days.

(21) Appl. No.: 17/254,725

(22) PCT Filed: Jun. 27, 2019

(86) PCT No.: PCT/US2019/039458
§ 371 (c)(1),
(2) Date: Dec. 21, 2020

(87) PCT Pub. No.: WO2020/006200
PCT Pub. Date: Jan. 2, 2020

(65) Prior Publication Data
US 2021/0269829 A1    Sep. 2, 2021

Related U.S. Application Data

(60) Provisional application No. 62/828,717, filed on Apr. 3, 2019, provisional application No. 62/691,359, filed on Jun. 28, 2018.

(51) Int. Cl.
| | | |
|---|---|---|
| *C12N 15/85* | (2006.01) | |
| *A61P 25/28* | (2006.01) | |
| *C12N 15/86* | (2006.01) | |
| *C07H 21/04* | (2006.01) | |

(52) U.S. Cl.
CPC ............ *C12N 15/86* (2013.01); *A61P 25/28* (2018.01); *C07H 21/04* (2013.01); *C12N 15/85* (2013.01); *C12N 2750/14143* (2013.01); *C12N 2830/008* (2013.01); *C12N 2830/50* (2013.01)

(58) Field of Classification Search
CPC ........ C12N 15/79; C12N 15/85; C12N 15/86; C12N 2750/14143; C12N 2830/008; C12N 2830/50; C12N 2800/22; C07H 21/04
See application file for complete search history.

(56) References Cited

U.S. PATENT DOCUMENTS

| | | |
|---|---|---|
| 4,501,729 A | 2/1985 | Boucher et al. |
| 5,399,346 A | 3/1995 | Anderson et al. |
| 5,478,745 A | 12/1995 | Samulski et al. |
| 6,040,183 A | 3/2000 | Ferrari et al. |
| 6,093,570 A | 7/2000 | Ferrari et al. |
| 6,156,303 A | 12/2000 | Russell et al. |
| 7,201,898 B2 | 4/2007 | Monahan et al. |
| 9,636,370 B2 | 5/2017 | McCown et al. |
| 2010/0047261 A1 | 2/2010 | Hoerr et al. |
| 2017/0360960 A1 | 12/2017 | Gray et al. |

FOREIGN PATENT DOCUMENTS

| | | |
|---|---|---|
| WO | 9811244 A2 | 3/1998 |
| WO | 9961601 A2 | 12/1999 |
| WO | 0017377 A2 | 3/2000 |
| WO | 0028004 A1 | 5/2000 |
| WO | 0028061 A2 | 5/2000 |
| WO | 0191803 A2 | 12/2001 |
| WO | 0192551 A2 | 12/2001 |
| WO | 2014152940 A1 | 9/2014 |
| WO | 2016172155 A1 | 10/2016 |
| WO | WO 2017/181021 A1 * | 10/2017 |
| WO | 2017218450 A1 | 12/2017 |
| WO | 2018045347 A1 | 3/2018 |
| WO | 2018089790 A1 | 5/2018 |

OTHER PUBLICATIONS

Savukoski et al., 1998 (Nature Genetics, vol. 19, p. 286-288).*
Amorim et al. "Molecular neuropathology of the synapse in sheep with CLN5 Batten disease" Brain and Behavior, 5 (11):e00401 (2015).
Bantel-Schaal et al. "Human Adeno-Associated Virus Type 5 Is Only Distantly Related to Other Known Primate Helper-Dependent Parvoviruses" Journal of Virology, 73(2):939-947 (1999).
Bosch et al. "Self-Complementary AAV9 Gene Delivery Partially Corrects Pathology Associated with Juvenile Neuronal Ceroid Lipofuscinosis (CLN3)" The Journal of Neuroscience, 36(37):9669-9682 (2016).
Chao et al. "Several Log Increase in Therapeutic Transgene Delivery by Distinct Adeno-Associated Viral Serotype Vectors" Molecular Therapy, 2(6):619-623 (2000).
Chiorini et al. "Cloning and Characterization of Adeno-Associated Virus Type 5" Journal of Virology, 73 (2):1309-1319 (1999).
Chiorini et al. "Cloning of Adeno-Associated Virus Type 4 (AAV4) and Generation of Recombinant AAV4 Particles" Journal of Virology, 71(9):6823-6833 (1997).
Conway et al. "High-titer recombinant adeno-associated virus production utilizing a recombinant herpes simplex virus type I vector expressing AAV-2 Rep and Cap" Gene Therapy, 6:986-993 (1999).
Cooper et al. "Towards a new understanding of NCL pathogenesis" Biochimica et Biophysica Acta, 1852:2256-2261 (2015).

(Continued)

*Primary Examiner* — Valerie E Bertoglio
(74) *Attorney, Agent, or Firm* — Myers Bigel, P.A.

(57) ABSTRACT

This invention relates to polynucleotides comprising optimized CLN5 open reading frame (ORF) sequences, vectors comprising the same, and methods of using the same for delivery of the ORF to a cell or a subject and to treat disorders associated with aberrant expression of a CLN5 gene or aberrant activity of a CLN5 gene product in the subject, such as CLN5 disease.

12 Claims, 8 Drawing Sheets

Specification includes a Sequence Listing.

(56) References Cited

OTHER PUBLICATIONS

Crystal et al. "Administration of a Replication-Deficient Adeno-Associated Virus Gene Transfer Vector Expressing the Human CLN2 cDNA to the Brain of Children with Late Infantile Neuronal Ceroid Lipofuscinosis" Human Gene Therapy, 15:1131-1154 (2004).
Ferrari et al. "New developments in the generation of Ad-free, high-titer rAAV gene therapy vectors" Nature Medicine, 3:1295-1297 (1997).
Frugier et al. "A new large animal model of CLN5 neuronal ceroid lipofuscinosis in Borderdale sheep is caused by a nucleotide substitution at a consensus splice site (c.571+1G>A) leading to excision of exon 3" Neurobiology of Disease, 29(2):306-315 (2008).
Gao et al. "Clades of Adeno-Associated Viruses Are Widely Disseminated in Human Tissues" Journal of Virology, 78 (12):6381-6388 (2004).
Gao et al. "Novel adeno-associated viruses from rhesus monkeys as vectors for human gene therapy" Proceedings of the National Academy of Sciences USA, 99(18):11854-11859 (2002).
GenBank Accession No. AF028704 "Adeno-associated virus 6, complete genome" www.ncbi.nlm.nih.gov (3 pages) (Jan. 12, 1998).
GenBank Accession No. AF028705 "Adeno-associated virus 3B, complete genome" www.ncbi.nlm.nih.gov (3 pages) (Jan. 12, 1998).
GenBank Accession No. AF043303 "Adeno-associated virus 2, complete genome" www.ncbi.nlm.nih.gov (4 pages) (May 20, 2010).
GenBank Accession No. AF063497 "Adeno-associated virus 1, complete genome" www.ncbi.nlm.nih.gov (3 pages) (Apr. 27, 1999).
GenBank Accession No. AF288061 "Hamster parvovirus 5' terminal hairpin gene sequence" www.ncbi.nlm.nih.gov (1 page) (Apr. 13, 2001).
GenBank Accession No. AF513851 "Adeno-associated virus 7 nonstructural protein and capsid protein genes, complete cds" www.ncbi.nlm.nih.gov (3 pages) (Sep. 5, 2002).
GenBank Accession No. AF513852 "Adeno-associated virus 8 nonstructural protein and capsid protein genes, complete cds" www.ncbi.nlm.nih.gov (3 pages) (Sep. 5, 2002).
GenBank Accession No. AH009962 "Hamster parvovirus" www.ncbi.nlm.nih.gov (2 pages) (Aug. 25, 2016).
GenBank Accession No. AX753250 "Sequence 5 from Patent EP1310571" www.ncbi.nlm.nih.gov (2 pages) (Jun. 23, 2003).
GenBank Accession No. AY028223 "B19 virus isolate patient_A.1.1 genomic sequence" www.ncbi.nlm.nih.gov (1 page) (Apr. 16, 2001).
GenBank Accession No. AY028226 "B19 virus isolate patient_A.2.1 genomic sequence" www.ncbi.nlm.nih.gov (1 page) (Apr. 16, 2001).
GenBank Accession No. AY530579 "Adeno-associated virus 9 isolate hu.14 capsid protein VP1 (cap) gene, complete cds" www.ncbi.nlm.nih.gov (2 pages) (Jun. 24, 2004).
GenBank Accession No. AY631966 "Adeno-associated virus 11 nonstructural protein and capsid protein genes, complete cds" www.ncbi.nlm.nih.gov (3 pages) (Nov. 30, 2004).
GenBank Accession No. EU285562 "Adeno-associated virus 13 nonstructural protein and capsid protein genes, complete cds" www.ncbi.nlm.nih.gov (3 pages) (Sep. 23, 2008).
GenBank Accession No. J01901 "Adeno-associated virus 2, complete genome" www.ncbi.nlm.nih.gov (3 pages) (Apr. 27, 1993).
GenBank Accession No. J02275 "Minute virus of mice, complete genome" www.ncbi.nlm.nih.gov (5 pages) (May 22, 1995).
GenBank Accession No. NC_000883 "Human parvovirus B19, complete genome" www.ncbi.nlm.nih.gov (4 pages) (Aug. 13, 2018).
GenBank Accession No. NC_001358 "Parvovirus H1, complete genome" www.ncbi.nlm.nih.gov (3 pages) (Feb. 10, 2015).
GenBank Accession No. NC_001401 "Adeno-associated virus—2, complete genome" www.ncbi.nlm.nih.gov (6 pages) (Aug. 13, 2018).
GenBank Accession No. NC_001510 "Minute virus of mice, complete genome" www.ncbi.nlm.nih.gov (5 pages) (Aug. 13, 2018).
GenBank Accession No. NC_001540 "Bovine parvovirus, complete genome" www.ncbi.nlm.nih.gov (4 pages) (Aug. 13, 2018).
GenBank Accession No. NC_001701 "Goose parvovirus, complete genome" www.ncbi.nlm.nih.gov (4 pages) (Aug. 13, 2018).
GenBank Accession No. NC_001729 "Adeno-associated virus—3, complete genome" www.ncbi.nlm.nih.gov (3 pages) (Aug. 13, 2018).
GenBank Accession No. NC_001829 "Adeno-associated virus—4, complete genome" www.ncbi.nlm.nih.gov (3 pages) (Aug. 13, 2018).
GenBank Accession No. NC_001862 "Adeno-associated virus 6, complete genome" www.ncbi.nlm.nih.gov (3 pages) (Jan. 12, 2004).
GenBank Accession No. NC_001863 "Adeno-associated virus 3B, complete genome" www.ncbi.nlm.nih.gov (3 pages) (Jan. 12, 2004).
GenBank Accession No. NC_002077 "Adeno-associated virus—1, complete genome" www.ncbi.nlm.nih.gov (3 pages) (Aug. 13, 2018).
GenBank Accession No. NC_006152 "Adeno-associated virus 5, complete genome" www.ncbi.nlm.nih.gov (3 pages) (Aug. 13, 2018).
GenBank Accession No. NC_006261 "Adeno-associated virus—8, complete genome" www.ncbi.nlm.nih.gov (3 pages) (Aug. 13, 2018).
GenBank Accession No. NM_001082595 "Ovis aries CLN5 intracellular trafficking protein (CLN5), mRNA" www.ncbi.nlm.nih.gov (3 pages) (Jul. 11, 2021).
GenBank Accession No. U89790 "Adeno-associated virus 4, complete genome" www.ncbi.nlm.nih.gov (3 pages) (Aug. 21, 1997).
GenBank Accession No. X01457 "Parvovirus h-1, complete genome" www.ncbi.nlm.nih.gov (3 pages) (Apr. 18, 2005).
Gray et al. "Optimizing Promoters for Recombinant Adeno-Associated Virus-Mediated Gene Expression in the Peripheral and Central Nervous System Using Self-Complementary Vectors" Human Gene Therapy, 22:1143-1153 (2011).
Gray et al. "Preclinical Differences of Intravascular AAV9 Delivery to Neurons and Glia: A Comparative Study of Adult Mice and Nonhuman Primates" Molecular Therapy, 19(6):1058-1069 (2011).
Gray et al. "Vector Design and Considerations for CNS Applications" Society for Neuroscience, pp. 1-9 (2011).
Hackett et al. "Safety of Direct Administration of AAV2CUhCLN2, a Candidate Treatment for the Central Nervous System Manifestations of Late Infantile Neuronal Ceroid Lipofuscinosis" Hum Gene Ther, 16:1484-1503 (2005).
Huber et al. "Cln5 is secreted and functions as a glycoside hydrolase in Dictyostelium" Cellular Signalling, 42:236-248 (2018).
Jolly et al. "Neuronal ceroid-lipofuscinosis in Borderdale sheep" New Zealand Veterinary Journal, 50(5):199-202 (2002).
Jules et al. "CLN5 is cleaved by members of the SPP/SPPL family to produce a mature soluble protein" Experimental Cell Research, 357:40-50 (2017).
Katz et al. "AAV gene transfer delays disease onset in a TPP1-deficient canine model of the late infantile form of Batten disease" Science Translational Medicine, 7(313):1-10 (2015).
Katz et al. "Enzyme Replacement Therapy Attenuates Disease Progression in a Canine Model of Late-Infantile Neuronal Ceroid Lipofuscinosis (CLN2 Disease)" Journal of Neuroscience Research, 92:1591-1598 (2014).
Linterman et al. "Lentiviral-Mediated Gene Transfer to the Sheep Brain: Implications for Gene Therapy in Batten Disease" Human Gene Therapy, 22:1011-1020 (2011).
Margolskee, R. F. "Epstein-Barr Virus Based Expression Vectors" Current Topics in Microbiology and Immunology, 158:67-95 (1992).
Marshall et al. "A clinical rating scale for Batten disease" Neurology, 65:275-279 (2005).
McCarty et al. "Self-complementary recombinant adeno-associated virus (scAAV) vectors promote efficient transduction independently of DNA synthesis" Gene Therapy, 8:1248-1254 (2001).
Mitchell et al. "Longitudinal In Vivo Monitoring of the CNS Demonstrates the Efficacy of Gene Therapy in a Sheep Model of CLN5 Batten Disease" Molecular Therapy, 26(10):2366-2378 (2018).
Mori et al. "Two novel adeno-associated viruses from cynomolgus monkey: pseudotyping characterization of capsid protein" Virology, 330:375-383 (2004).

(56) References Cited

OTHER PUBLICATIONS

Muramatsu et al. "Nucleotide Sequencing and Generation of an Infectious Clone of Adeno-Associated Virus 3" Virology, 221(1):208-217 (1996).

Neverman et al. "Experimental therapies in the neuronal ceroid lipofuscinoses" Biochimica et Biophysica Acta, 1852:2292-2300 (2015).

Palmer et al. "Recent studies of ovine neuronal ceroid lipofuscinoses from BARN, the Batten Animal Research Network" Biochimica et Biophysica Acta, 1852:2279-2286 (2015).

Palombo et al. "Site-Specific Integration in Mammalian Cells Mediated by a New Hybrid Baculovirus-Adeno-Associated Virus Vector" Journal of Virology, 72(6):5025-5034 (1998).

Ruffing et al. "Mutations in the carboxy terminus of adeno-associated virus 2 capsid proteins affect viral infectivity: lack of an RGD integrin-binding motif" Journal of General Virology, 75:3385-3392 (1994).

Rutledge et al. "Infectious Clones and Vectors Derived from Adeno-Associated Virus (AAV) Serotypes Other Than AAV Type 2" Journal of Virology, 72(1):309-319 (1998).

Schmidt et al. "Molecular Characterization of the Heparin-Dependent Transduction Domain on the Capsid of a Novel Adeno-Associated Virus Isolate, AAV(VR-942)" Journal of Virology, 82(17):8911-8916 (2008).

Shade et al. "Nucleotide Sequence and Genome Organization of Human Parvovirus B19 Isolated from the Serum of a Child during Aplastic Crisis" Journal of Virology, 58(3):921-936 (1986).

Simonati et al. "Phenotype and natural history of variant late infantile ceroid-lipofuscinosis 5" Developmental Medicine & Child Neurology, 59:815-821 (2017).

Sleat et al. "Mass Spectrometry-based Protein Profiling to Determine the Cause of Lysosomal Storage Diseases of Unknown Etiology" Molecular & Cellular Proteomics, 8:1708-1718 (2009).

Sondhi et al. "AAV2-mediated CLN2 gene transfer to rodent and non-human primate brain results in long-term TPP-I expression compatible with therapy for LINCL" Gene Therapy, 12:1618-1632 (2005).

Sondhi et al. "Enhanced Survival of the LINCL Mouse Following CLN2 Gene Transfer Using the rh.10 Rhesus Macaque-derived Adeno-associated Virus Vector" Molecular Therapy, 15(3):481-491 (2007).

Sondhi et al. "Long-Term Expression and Safety of Administration of AAVrh.10hCLN2 to the Brain of Rats and Nonhuman Primates for the Treatment of Late Infantile Neuronal Ceroid Lipofuscinosis" Human Gene Therapy, 23:324-335 (2012).

Srivastava et al. "Nucleotide Sequence and Organization of the Adeno-Associated Virus 2 Genome" Journal of Virology, 45(2):555-564 (1983).

Urabe et al. "Insect Cells as a Factory to Produce Adeno-Associated Virus Type 2 Vectors" Human Gene Therapy, 13:1935-1943 (2002).

Xiao et al. "Gene Therapy Vectors Based on Adeno-Associated Virus Type 1" Journal of Virology, 73(5):3994-4003 (1999).

Yang et al. "Virus-Mediated Transduction of Murine Retina with Adeno-Associated Virus: Effects of Viral Capsid and Genome Size" Journal of Virology, 76(15):7651-7660 (2002).

Zhang et al. "Recombinant adenovirus expressing adeno-associated virus cap and rep proteins supports production of hightiter recombinant adeno-associated virus" Gene Therapy, 8:704-712 (2001).

Zolotukhin et al. "Recombinant adeno-associated virus purification using novel methods improves infectious titer and yield" Gene Therapy, 6:973-985 (1999).

International Search Report and Written Opinion corresponding to PCT/US2019/039458, dated Oct. 29, 2019, 11 pages.

Colella et al. "Emerging Issues in AAV-Mediated In Vivo Gene Therapy" Molecular Therapy Methods & Clinical Development, 8:87-104 (2018).

Extended European Search Report corresponding to European Patent Application No. 19826972.2 (9 pages) (dated Mar. 14, 2022).

Hughes et al. "Inhibition of storage pathology in prenatal CLN5-deficient sheep neural cultures by lentiviral gene therapy" Neurobiology of Disease, 62:543-550 (2014).

Russell, Katharina Natalie "Longitudinal in vivo monitoring of the neuropathy in ovine neuronal ceroid lipofuscinoses" A thesis submitted in partial fulfilment of the requirements for the Degree of Doctor of Philosophy, Lincoln University, 146 pages (2017).

"Eudravigilance: Electronic Reporting." European Medicines Agency (EMA), www.ema.europa.eu/en/human-regulatory-overview/research-development/pharmacovigilance-research-development/eudravigilance/eudravigilance-electronic-reporting. Accessed Nov. 7, 2024.

Amicus Therapeutics, "Gene Therapy for Children With CLN3 Batten Disease", Accessed on Feb. 25, 2021 from https://clinicaltrials.gov/ct2/show/NCT03770572.

Amicus Therapeutics, "Gene Therapy for Children With Variant Late Infantile Neuronal Ceroid Lipofuscinosis 6 (vLINCL6) Disease", Accessed on Feb. 25, 2021 from https://clinicaltrials.gov/ct2/show/NCT02725580.

ClinicalTrials.gov ID: NCT02122952 "Gene Transfer Clinical Trial for Spinal Muscular Atrophy Type 1" Study record accessed on Mar. 8, 2021 from https://www.clinicaltrials.gov.

ClinicalTrials.gov ID: NCT02362438 "Intrathecal Administration of scAAV9/JeT-GAN for the Treatment of Giant Axonal Neuropathy" Study record accessed on Mar. 8, 2021 from https://www.clinicaltrials.gov.

ClinicalTrials.gov ID: NCT02716246 "Phase I/II/III Gene Transfer Clinical Trial of scAAV9.U1a.hSGSH" Study record accessed on Mar. 8, 2021 from https://www.clinicaltrials.gov.

ClinicalTrials.gov ID: NCT03315182 "Gene Transfer Clinical Trial for Mucopolysaccharidosis (Mps) Iiib (Mpsiiib)" Study record accessed on Mar. 8, 2021 from https://www.clinicaltrials.gov.

ClinicalTrials.gov ID: NCT03822650 "A Natural History Study of Neuronal Ceroid Lipofuscinosis Type 5 (CLN5)" Study record accessed on Mar. 8, 2021 from https://www.clinicaltrials.gov.

European Medicines Agency, "MabThera (rituximab) Summary of Product Characteristics", 1998. efaidnbmnnnibpcajpcglclefindmkaj/https://www.ema.europa.eu/en/documents/product-information/mabthera-epar-product-information_en.pdf.

European Medicines Agency, "Rapamune® (sirolimus) Summary of Product Characteristics", efaidnbmnnnibpcajpcglclefindmkaj/https://www.ema.europa.eu/en/documents/product-information/rapamune-epar-product-information_en.pdf.

FDA, "Rapamune® (sirolimus) United States Prescribing Information", 2017, https://www.accessdata.fda.gov/drugsatfda_docs/label/2017/021083s059,021110s076lbl.pdf.

FDA, "Rituxan (rituximab) United States Prescribing Information" 1997, https://www.accessdata.fda.gov/drugsatfda_docs/label/2010/103705s5311lbl.pdf.

National Institute of Neurological Disorders and Stroke. Batten Disease Fact Sheet. Accessed on Mar. 5, 2021 from https://www.clinicaltrials.gov.

Uniprot, "Bis(monoacylglycero)phosphate synthase CLN5" 075503 (CLN5_Human). (updated Apr. 29, 2008) Available at: https://www.uniprot.org/uniprotkb/O75503/entry.

University of Central London, "Gene Mutation Table", http://www.ucl.ac.uk/ncl/CLN5mutationtable.htm. Accessed on Apr. 23, 2021.

US Department of Health and Human Services, "Common Terminology Criteria for Adverse Events (CTCAE), Version 5.0", Published: Nov. 27, 2017.

Weill Medical College of Cornell University, "Safety Study of a Gene Transfer Vector (Rh. 10) for Children With Late Infantile Neuronal Ceroid Lipofuscinosis (LINCL)", https://clinicaltrials.gov/study/NCT01161576 (Feb. 2, 2021).

Weill Medical College of Cornell University, "Safety Study of a Gene Transfer Vector for Children With Late Infantile Neuronal Ceroid Lipofuscinosis", https://clinicaltrials.gov/study/NCT00151216 (Jul. 24, 2020).

"National Cancer Institute. Common terminology criteria for adverse events (CTCAE) version 5.0.", US Department of Health and Human Services., Accessed on Feb. 25, 2021 from https://ctep.cancer.gov/protocoldevelopment/electronic_applications/docs/ctcae_v5_quic k_reference_5x7.pdf.

(56) References Cited

OTHER PUBLICATIONS

Aljebab, et al., "Systematic review of the toxicity of long-course oral corticosteroids in children", PloS One, 12(1): e0170259 (2017).

Autti, et al., "MRI of neuronal ceroid lipofuscinosis: I. Cranial MRI of 30 patients with juvenile neuronal ceroid lipofuscinosis", Neuroradiology, 38:476-482 (1996).

Azad, et al., "Novel likely disease-causing CLN5 variants identified in Pakistani patients with neuronal ceroid lipofuscinosis", Journal of the Neurological Sciences, 414:116826 (2020).

Basak, et al., "A lysosomal enigma CLN5 and its significance in understanding neuronal ceroid lipofuscinosis", Cellular and Molecular Life Sciences, 78:4735-4763 (2021).

Bekerman, et al., "Variations in eyeball diameters of the healthy adults", Journal of Ophthalmology, 2014 (503645): 1-5 (2014).

Bessa, et al., "Two novel CLN5 mutations in a Portuguese patient with vLINCL: insights into molecular mechanisms of CLN5 deficiency", Molecular Genetics and Metabolism, 89:245-253 (2006).

Bharucha-Goebel, et al., "Immune analysis following intrathecal gene transfer: 3 year data from clinical intrathecal gene transfer trial for patients with Giant Axonal Neuropathy", Molecular Therapy, 27(4S1):298-299 (2019).

Bouquet, et al., "Immune response and intraocular inflammation in patients with Leber hereditary optic neuropathy treated with intravitreal injection of recombinant adeno-associated virus 2 carrying the ND4 gene: a secondary analysis of a phase 1/2 clinical trial", JAMA Ophthalmology, 137(4):399-406 (2019).

Burcham, et al., "Immunosuppression drug therapy in lung transplantation for cystic fibrosis", Pediatric Drugs, 19:339-346 (2017).

Chand, et al., "Thrombotic microangiopathy following onasemnogene abeparvovec for spinal muscular atrophy: a case series", The Journal of Pediatrics, 231:265-268 (2021).

Chau, et al., "Is eye size related to orbit size in human subjects?", Ophthalmic and Physiological Optics, 24:35-40 (2004).

Chau, et al., "Orbital development in Hong Kong Chinese subjects", Ophthalmic and Physiological Optics, 24:436-439 (2004).

Choudhury, et al., "Viral vectors for therapy of neurologic diseases", Neuropharmacology, 120:63-80 (2017).

Cukras, et al., "Retinal AAV8-RS1 gene therapy for X-linked retinoschisis: initial findings from a phase I/IIa trial by intravitreal delivery", Molecular Therapy, 26(9):2282-2294 (2018).

Dekaban, et al., "Changes in brain weights during the span of human life: relation of brain weights to body heights and body weights", Annals of Neurology: Official Journal of the American Neurological Association and the Child Neurology Society, 4(4):345-356 (1978).

Gan, et al., "Psychometric properties of functional balance assessment in children with cerebral palsy", Neurorehabilitation and Neural Repair, 22(6):745-753 (2008).

Garfield, et al., "Development of a brief, generic, modular resource-use measure (ModRUM): cognitive interviews with patients", BMC Health Services Research, 21:1-12 (2021).

Ge, et al., "Novel mutations in CLN5 of Chinese Patients with neuronal ceroid lipofuscinosis", Journal of Child Neurology, 33(13):837-850 (2018).

Gordon, et al., "Refractive development of the human eye", Archives of Ophthalmology, 103(6):785-789 (1985).

Grobe-Einsler, et al., "Development of SARAhome, a new video-based tool for the assessment of ataxia at home", Movement Disorders, 36(5):1242-1246 (2021).

Guillou, et al., "Fatal thrombotic microangiopathy case following adeno-associated viral SMN gene therapy", Blood Advances, 6(14):4266-4270 (2022).

Heinonen, et al., "CLN-1 and CLN-5, genes for infantile and variant late infantile neuronal ceroid lipofuscinoses, are expressed in the embryonic human brain", Journal of Comparative Neurology, 426(3):406-412 (2000).

Herrera, et al., "Choroidal thickness and vol. in a healthy pediatric population and its relationship with age, axial length, ametropia, and sex", Retina, 35(12):2574-2583 (2015).

Holmberg, et al., "Phenotype-genotype correlation in eight patients with Finnish variant late infantile NCL (CLN5)", Neurology, 55(4):579-581 (2000).

Holmberg, et al., "The mouse ortholog of the neuronal ceroid lipofuscinosis CLN5 gene encodes a soluble lysosomal glycoprotein expressed in the developing brain", Neurobiology of Disease, 16(1):29-40 (2004).

Howland, et al., "The allometry and scaling of the size of vertebrate eyes", Vision Research, 44(17):2043-2065 (2004).

Hudry, et al., "Therapeutic AAV gene transfer to the nervous system: a clinical reality", Neuron, 101(5):839-862 (2019).

Hughes, et al., "AAV9 intracerebroventricular gene therapy improves lifespan, locomotor function and pathology in a mouse model of Niemann-Pick type C1 disease", Human Molecular Genetics, 27(17):3079-3098 (2018).

Ibinaiye, et al., "Estimation of the eyeball vol. on magnetic resonance images in Zaria, Nigeria", Sub-Saharan African Journal of Medicine, 1(2):82-85 (2014).

Isosomppi, et al., "Lysosomal localization of the neuronal ceroid lipofuscinosis CLN5 protein", Human Molecular Genetics, 11(8):885-891 (2002).

Jamois, et al., "Rituximab pediatric drug development: pharmacokinetic and pharmacodynamic modeling to inform regulatory approval for rituximab treatment in patients with granulomatosis with polyangiitis or microscopic polyangiitis", Clinical and Translational Science, 15(9):2172-2183 (2022).

Jolly, et al., "Mitochondrial dysfunction in the neuronal ceroid-lipofuscinoses (Batten disease)", Neurochemistry International, 40(6):565-571 (2002).

Kassirer, et al., "Controversial journal editorials", New England Journal of Medicine, 337(20):1460-1461 (1997).

Kassirer, et al., "On authorship and acknowledgments", New England Journal of Medicine, 325(21):510-512 (1991).

Katz-Leurer, et al., "Functional balance tests for children with traumatic brain injury: within-session reliability", Pediatric Physical Therapy, 20(3):254-258 (2008).

Kishimoto, et al., "Addressing high dose AAV toxicity—'one and done' or 'slower and lower'?", Expert Opinion on Biological Therapy, 22(9):1067-1071 (2022).

Kopra, et al., "A mouse model for Finnish variant late infantile neuronal ceroid lipofuscinosis, CLN5, reveals neuropathology associated with early aging", Human Molecular Genetics, 13(23):2893-2906 (2004).

Kousi, et al., "Mutations in CLN7/MFSD8 are a common cause of variant late-infantile neuronal ceroid lipofuscinosis", Brain, 132:810-819 (2009).

Leinonen, et al., "Retinal degeneration in a mouse model of CLN5 disease is associated with compromised autophagy", Scientific Reports, 7(1):1597 (2017).

Liu, et al., "A practical guide to the monitoring and management of the complications of systemic corticosteroid therapy", Allergy, Asthma & Clinical Immunology, 9:1-25 (2013).

Luo, et al., "Functional analysis of a novel CLN5 mutation identified in a patient with neuronal ceroid lipofuscinosis", Frontiers in Genetics, 11:536221 (2020).

Mcatee, et al., "Association of rituximab use with adverse events in children, adolescents, and young adults", JAMA Network Open, 4(2):e2036321-e2036321 (2021).

Medoh, et al., "The Batten disease gene product CLN5 is the lysosomal bis (monoacylglycero) phosphate synthase", Science, 381(6663):1182-1189 (2023).

Mendell, et al., "Single-dose gene-replacement therapy for spinal muscular atrophy", New England Journal of Medicine, 377(18):1713-1722 (2017).

Mingozzi, et al., "Overcoming the Host Immune Response to Adeno-Associated Virus Gene Delivery Vectors: The Race Between Clearance, Tolerance, Neutralization, and Escape", Annual Review of Virology 4(1):511-534 (2017).

Mole, et al., "Genetics of the Neuronal Ceroid Lipofuscinoses (Batten disease)", Biochimica et Biophysica Acta, 1852 (10):2237-2241 (2015).

Mole, et al., "Neuronal Ceroid-Lipofuscinoses", Retired chapter, for historical reference only, Gene Reviews (2013).

(56) References Cited

OTHER PUBLICATIONS

Moore, et al., "The clinical and genetic epidemiology of neuronal ceroid lipofuscinosis in Newfoundland", Clinical Genetics, 74(3):213-222 (2008).
Murray, et al., "Natural history of retinal degeneration in ovine models of CLN5 and CLN6 neuronal ceroid lipofuscinoses", Scientific Reports, 12(1):3670 (2022).
Peruzzi, et al., "Challenges in pediatric renal transplantation", World Journal of Transplantation, 4(4):222 (2014).
Picaud, et al., "The primate model for understanding and restoring vision", Proceedings of the National Academy of Sciences, 116(52):26280-26287 (2019).
Podsiadlo, et al., "The timed "Up & Go": a test of basic functional mobility for frail elderly persons", Journal of the American Geriatrics Society, 39(2):142-148 (1991).
Qureshi, et al., "An Alzheimer's disease-linked loss-of-function CLN5 variant impairs cathepsin D maturation, consistent with a retromer trafficking defect", Molecular and Cellular Biology, 38(20):e00011-18 (2018).
Radke, et al., "Human NCL neuropathology", Biochimica et Biophysica Acta, 1852(10):2262-2266 (2015).
Ren, et al., "Next-generation sequencing analysis reveals novel pathogenic variants in four Chinese siblings with late-infantile neuronal ceroid lipofuscinosis", Frontiers in Genetics, 10:370 (2019).
Ronzitti, et al., "Human immune responses to adeno-associated virus (AAV) vectors", Frontiers in Immunology, 11:670 (2020).
Rubin, et al., "2013 IDSA clinical practice guideline for vaccination of the immunocompromised host", Clinical Infectious Diseases, 58(3):e44-e100 (2014).
Russell, et al., "Electroretinography data from ovine models of CLN5 and CLN6 neuronal ceroid lipofuscinoses", Data in Brief, 37:107188 (2021).
Saraiva, et al., "Gene therapy for the CNS using AAVs: the impact of systemic delivery by AAV9", Journal of Controlled Release, 241:94-109 (2016).
Schmitz-Hubsch, et al., "Scale for the assessment and rating of ataxia: development of a new clinical scale", Neurology, 66(11):1717-1720 (2006).
Schulz, et al., "Study of intraventricular cerliponase alfa for CLN2 disease", New England Journal of Medicine, 378(20):1898-1907 (2018).
Shen, et al., "rAAV immunogenicity, toxicity, and durability in 255 clinical trials: A meta-analysis", Frontiers in Immunology, 13:1001263 (2022).
Sigurdsson, et al., "Six commonly used empirical body surface area formulas disagreed in young children undergoing corrective heart surgery", Acta Paediatrica, 109(9):1838-1846 (2020).
Steinle, et al., "Impact of baseline characteristics on geographic atrophy progression in the FILLY trial evaluating the complement C3 inhibitor pegcetacoplan", American Journal of Ophthalmology, 227:116-124 (2021).
Summa, et al., "Development of SaraHome: A novel, well-accepted, technology-based assessment tool for patients with ataxia", Computer Methods and Programs in Biomedicine, 188:105257 (2020).
Tönshoff, Burkhard, "Immunosuppressive therapy post-transplantation in children: what the clinician needs to know", Expert Review of Clinical Immunology, 16(2):139-154 (2020).
Tyynelä, et al., "Hippocampal pathology in the human neuronal ceroid-lipofuscinoses: distinct patterns of storage deposition, neurodegeneration and glial activation", Brain Pathology, 14(4):349-357 (2004).
Tyynelä, et al., "Variant late infantile neuronal ceroid-lipofuscinosis: pathology and biochemistry", Journal of Neuropathology & Experimental Neurology, 56(4):369-375 (1997).
Wan, et al., "Efficacy and safety of rAAV2-ND4 treatment for Leber's hereditary optic neuropathy", Scientific Reports, 6(1):21587 (2016).
Williams, et al., "Investigation of the timed 'up & go' test in children", Developmental Medicine and Child Neurology, 47(8):518-524 (2005).
Xin, et al., "CLN5 mutations are frequent in juvenile and late-onset non-Finnish patients with NCL", Neurology, 74 (7):565-571 (2010).
Yin, et al., "Intravitreal injection of AAV2 transduces macaque inner retina", Investigative Ophthalmology & Visual Science, 52(5):2775-2783 (2011).

* cited by examiner

CONTROL CLN5+/- 8 mo.

UNTREATED CLN5-/- 8 mo.

UNTREATED CLN5-/- 19 mo.

scAAV9 TREATED 19 mo.

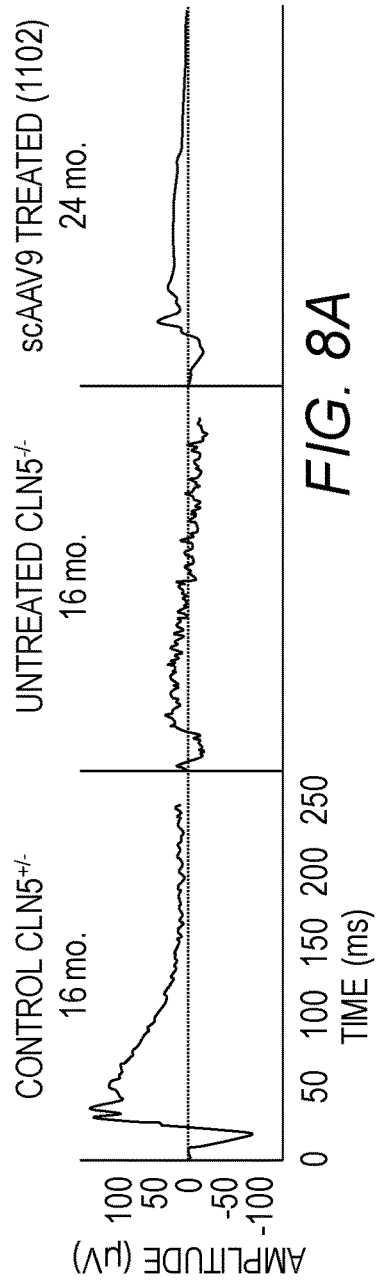
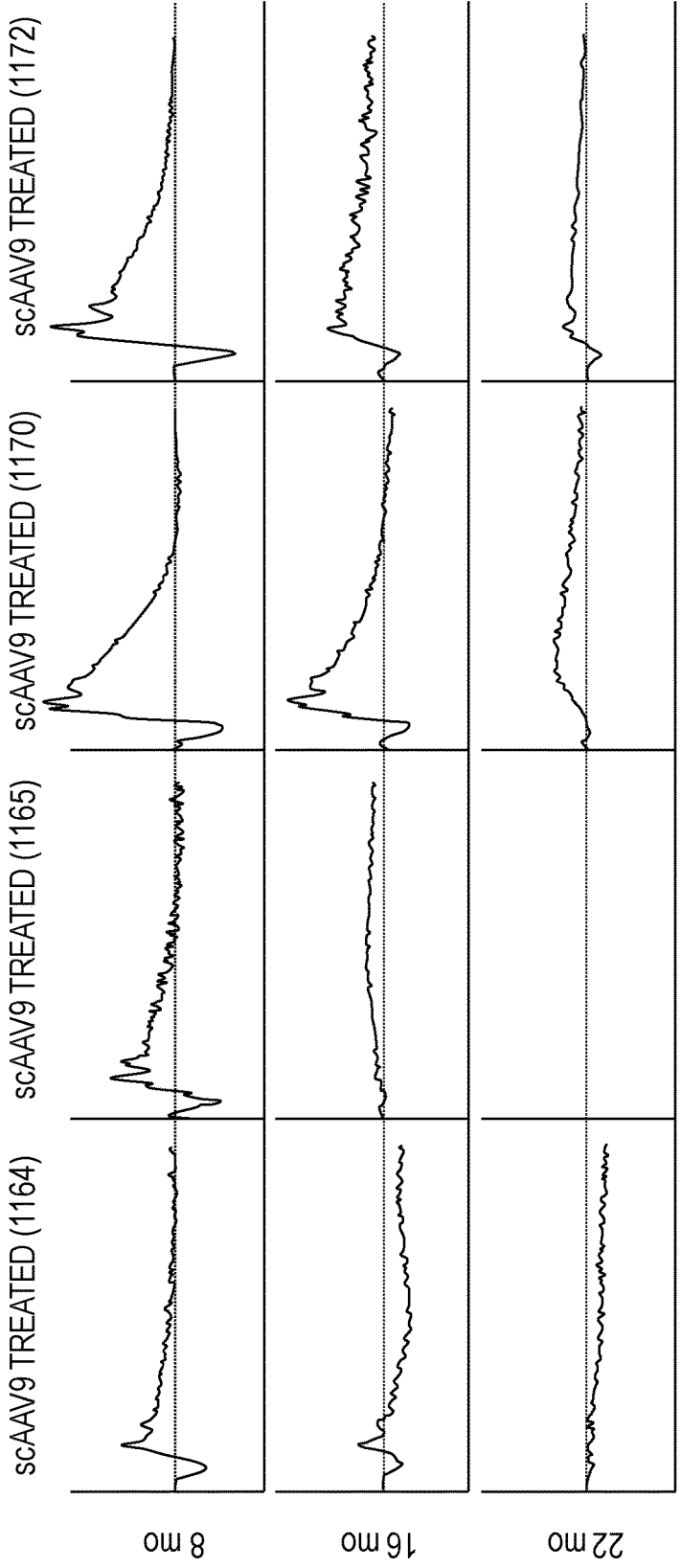
FIG. 8A
FIG. 8B

SEQUENCE LISTING

<160> NUMBER OF SEQ ID NOS: 11

<210> SEQ ID NO 1
<211> LENGTH: 1077
<212> TYPE: DNA
<213> ORGANISM: Artificial
<220> FEATURE:
<223> OTHER INFORMATION: human CLN5 ORF

<400> SEQUENCE: 1

```
atggcgcagg aggtggacac tgcacagggg gccgagatga gaagaggagc cggagcagct      60
agaggacggg ccagctggtg ttgggccttg gcgctgctct ggctggctgt ggtgcctggc     120
tggtccagag tgtccgggat tccctcgagg cgccattggc ctgtgccata taagcgcttc     180
gacttccggc ctaagcccga cccgtactgc caggccaagt acaccttttg tcccaccgga     240
tcgcccatcc ctgtgatgga gggcgacgat gacatcgaag tgttccgact gcaagccccc     300
gtgtgggaat tcaaatacgg cgaccttctg ggccacctga agatcatgca tgacgccatc     360
gggttccgct cgaccctgac cggaaagaac tacaccatgg agtggtacga actgttccag     420
ctgggaaact gcaccttccc tcaccttcgg cctgaaatgg atgcaccttt ctggtgcaac     480
caaggcgctg cctgcttctt tgaggggatc gacgatgtgc actggaagga gaacggaacc     540
ctggtccaag tggccactat ctccgggaac atgttcaacc agatggccaa atgggtgaag     600
caggataatg agactggcat ctactatgaa acttggaacg tgaaagccag cccggagaag     660
ggtgccgaaa cctggttcga ttcctacgac tgctccaagt tcgtgctgcg gaccttcaac     720
aagctggccg agttcggtgc cgagttcaag aacattgaaa ccaactacac tcgcattttc     780
ctctactcgg gcgaacccac ctacctggga aacgaaacta gcgtctttgg gccgactgga     840
aacaagactt tggggctcgc gatcaagagg ttctactacc ctttcaagcc gcaccttccg     900
accaaggaat tcttgctgag cctgctgcag attttcgatg ccgtgatcgt gcataagcag     960
ttctatctgt tttacaattt cgaatactgg ttcctcccga tgaagttccc gttcattaag    1020
atcacctacg aggaaatccc actcccgatc cgcaacaaga ccctgtccgg tctgtaa       1077
```

<210> SEQ ID NO 2
<211> LENGTH: 1089
<212> TYPE: DNA
<213> ORGANISM: Artificial

```
<220> FEATURE:
<223> OTHER INFORMATION: ovine CLN5 ORF

<400> SEQUENCE: 2
atggcacaag caggaggagc aggggcagga gcttggggaa ggagaggagc aggagctgga      60
gcgggccctg agcgggcccc ttggcgctgg gccccggccc tgctgtggct cgcggcggct     120
actgccgctg ccgccgccgc cggggacccg tcccggagac agtggccggt gccatacaag     180
cgcttcagct tcggcccgga ccggacccg tactgtcagg ccaagtacac cttctgccca      240
accggctccc ctatcccggt catgaaggac gacgacgtca ttgaagtgtt caggctccaa     300
gcccccgtgt gggagttcaa atacggagat ctgcttggtc acttgaagat tatgcacgat     360
gcgatcggct ttcgctccac cctgaccgag aagaactaca ctatggagtg gtacgaattg     420
ttccagctgg gcaactgcac ttttcccccac ctgaggcccg agatgaacgc gcctttctgg    480
tgtaaccagg gtgcagcctg ctttttcgag ggcatcgacg acaaccattg aaggagaac      540 ggcacccctgg tcctggtggc acaatcagc ggcgggatgt caacaagat ggccaaatgg      600 gtgaagcagg acaacgagac tggaatctat tacgagactt ggaccgtgca agcctcaccc    660
aagaaggagg ccgagaagtg gttcgagtcc tacgactgct caaagttcgt gctgcgcacc    720
tacgaaaagc tggccgaact ggagccgac ttcaagaaga tcgaaaccaa ctacacccgc     780
atctttctgt attcgggcga acccacgtac ctgggaaacg aaacctccgt gttcggccct    840
accgggaaca agactcttgc tctcgccatc aagaagttct actaccgtt caagccgcac     900 ctgtcgacca aggaattcct cctgagcctg ctgcagatct tgatgcggt ggtcattcac     960 cgggaattct atctgttcta caatttcgag tactggttcc tccctatgaa atccccattc   1020
attaagatca cttacgaaga aattccgctc cccaatcgca aaaaccggac cctgtccggt   1080
ctgtgataa                                                           1089

<210> SEQ ID NO 3
<211> LENGTH: 306
<212> TYPE: DNA
<213> ORGANISM: Artificial
<220> FEATURE:
<223> OTHER INFORMATION: chicken beta actin promoter

<400> SEQUENCE: 3
tacgtattag tcatcgctat taccatggtc gaggtgagcc ccacgttctg cttcactctc      60
cccatctccc cccctccccc acccccaatt ttgtatttat ttatttttta attattttgt     120
gcagcgatgg gggcgggggg ggggggggggg cgcgcgccag gcggggcggg gcggggcgag    180
ggcgggggcg gggcgaggcg gagaggtgcg gcggcagcca atcagagcgg cgcgctccga    240
aagtttcctt ttatggcgag gcggcggcgg cggcggccct ataaaaagcg aagcgcgcgg    300
cgggcg                                                              306

<210> SEQ ID NO 4
<211> LENGTH: 137
<212> TYPE: DNA
<213> ORGANISM: Artificial
<220> FEATURE:
<223> OTHER INFORMATION: Chimeric intron

<400> SEQUENCE: 4
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc    120
```

```
tccgggctgt aattagc                                                137
```

<210> SEQ ID NO 5
<211> LENGTH: 1881
<212> TYPE: DNA
<213> ORGANISM: Artificial
<220> FEATURE:
<223> OTHER INFORMATION: CAGGS promoter

<400> SEQUENCE: 5

```
gatctgaatt cggatcttca atattggcca ttagccatat tattcattgg ttatatagca    60
taaatcaata ttggatattg gccattgcat acgttgtatc tatatcataa tatgtacatt   120
tatattggct catgtccaat atgaccgcca tgttggcatt gattattgac tagttattaa   180
tagtaatcaa ttacgggtc  attagttcat agcccatata tggagttccg cgttacataa   240
cttacggtaa atggcccgcc tggctgaccg cccaacgacc cccgcccatt gacgtcaata   300
atgacgtatg ttcccatagt aacgccaata gggactttcc attgacgtca atgggtggag   360
tatttacggt aaactgccca cttggcagta catcaagtgt atcatatgcc aagtccgccc   420
cctattgacg tcaatgacgg taaatggccc gcctggcatt atgcccagta catgacctta   480
cgggactttc ctacttggca gtacatctac gtattagtca tcgctattac catggtcgag   540
gtgagcccca cgttctgctt cactctcccc atctccccccc cctccccacc cccaattttg   600
tatttattta ttttttaatt attttgtgca gcgatggggg cggggggggg ggggggcgc    660
gcgccaggcg gggcggggcg gggcgagggg cggggcgggg cgaggcggag aggtgcggcg   720
gcagccaatc agagcggcgc gctccgaaag tttccttta  tggcgaggcg gcggcggcg    780
cggccctata aaaagcgaag cgcgcggcgg gcgggagtcg ctgcgacgct gccttcgccc   840
cgtgccccgc tccgccgccg cctcgcgccg cccgccccgg ctctgactga ccgcgttact   900
cccacaggtg agcgggcggg acggcccttc cctccgggc  tgtaattagc gcttggttta   960
atgacggctt gtttcttttc tgtggctgcg tgaaagcctt gaggggctcc gggagggccc  1020
tttgtgcggg gggagcggc  tcgggggtg  cgtgcgtgtg tgtgtgcgtg gggagcgccg  1080
cgtgcggccc gcgctgcccg gcggctgtga gcgctgcggg cgcggcgcgg gctttgtgc   1140
gctccgcagt gtgcgcgagg ggagcgcggc cggggcggt  gccccgcggt gcggggggg   1200
ctgcgagggg aacaaaggct gcgtgcgggg tgtgtgcgtg ggggggtgag caggggtat   1260
gggcgcggcg gtcgggctgt aacccccccc tgcaccccc  tccccgagtt gctgagcacg  1320
gcccggcttc gggtgcgggg ctccgtacgg ggcgtggcgc ggggctcgcc gtgccgggcg  1380
gggggtggcg gcaggtgggg gtgccgggcg ggcgggggcc gcctcgggcc gggagggct   1440
cgggggaggg gcgcggcggc ccccggagcg ccggcggctg tcgaggcgcg gcgagccgca  1500
gccattgcct tttatggtaa tcgtgcgaga gggcgcaggg acttactttg tcccaaatct  1560
gtgcggagcc gaaatctggg aggcgccgcc gcacccctc  tagcgggcgc ggggcgaagc  1620
ggtgcggcgc cggcaggaag gaaatgggcg gggagggcct tcgtgcgtcg ccgcgccgcc  1680
gtccccttct ccctctccag cctcggggct gtccgcgggg gacggctgc  cttcggggg   1740
gacggggcag ggcggggttc ggcttctggc gtgtgaccgg cggctctaga gcctctgcta  1800
accatgttca tgccttcttc tttttcctac agctcctggg caacgtgctg gttattgtgc  1860
tgtctcatca ttttggcaaa g                                            1881
```

<210> SEQ ID NO 6
<211> LENGTH: 256

```
<212> TYPE: DNA
<213> ORGANISM: Artificial
<220> FEATURE:
<223> OTHER INFORMATION: CMV enhancer

<400> SEQUENCE: 6
tacataactt acggtaaatg cccgcctgg ctgaccgccc aacgacccc gcccattgac      60 gtcaatagta acgccaatag ggactttcca ttgacgtcaa tgggtggagt atttacggta     120
aactgcccac ttggcagtac atcaagtgta tcatatgcca agtacgcccc ctattgacgt    180
caatgacggt aaatggcccg cctggcattg tgcccagtac atgaccttat gggactttcc    240
tacttggcag tacatc                                                     256

<210> SEQ ID NO 7
<211> LENGTH: 48
<212> TYPE: DNA
<213> ORGANISM: Artificial
<220> FEATURE:
<223> OTHER INFORMATION: SpA

<400> SEQUENCE: 7
aataaagagc tcagatgcat cgatcagagt gtgttggttt tttgtgtg                   48

<210> SEQ ID NO 8
<211> LENGTH: 143
<212> TYPE: DNA
<213> ORGANISM: Artificial
<220> FEATURE:
<223> OTHER INFORMATION: SV40pA

<400> SEQUENCE: 8
agacatgata agatacattg atgagtttgg acaaaccaca actagaatgc agtgaaaaaa      60
atgctttatt tgtgaaattt gtgatgctat tgctttattt gtaaccatta taagctgcaa    120
taaacaagtt aacaacaaca att                                             143

<210> SEQ ID NO 9
<211> LENGTH: 254
<212> TYPE: DNA
<213> ORGANISM: Artificial
<220> FEATURE:
<223> OTHER INFORMATION: BGHpA

<400> SEQUENCE: 9
ctcgactgtg ccttctagtt gccagccatc tgttgtttgc ccctcccccg tgccttcctt      60
gaccctggaa ggtgccactc ccactgtcct ttcctaataa aatgaggaaa ttgcatcgca    120
ttgtctgagt aggtgtcatt ctattctggg gggtggggtg ggcaggaca gcaaggggga     180 ggattgggaa gacaacagca ggcatgctgg ggatgcggtg gctctatgg cttctgaggc     240 ggaaagaacc agct                                                       254

<210> SEQ ID NO 10
<211> LENGTH: 2176
<212> TYPE: DNA
<213> ORGANISM: Artificial
<220> FEATURE:
<223> OTHER INFORMATION: Human CLN5 cassette

<400> SEQUENCE: 10
tacataactt acggtaaatg cccgcctgg ctgaccgccc aacgacccc gcccattgac       60 gtcaataatg acgtatgttc ccatagtaac gccaataggg actttccatt gacgtcaatg   120
```

```
ggtggagtat ttacggtaaa ctgcccactt ggcagtacat caagtgtatc atatgccaag    180
tacgcccct attgacgtca atgacggtaa atggcccgcc tggcattatg cccagtacat     240
gaccttatgg gactttccta cttggcagta catctacgta ttagtcatcg ctattaccat    300
ggtcgaggtg agccccacgt tctgcttcac tctccccatc tccccccct cccccaccccc    360
aattttgtat ttatttattt tttaattatt ttgtgcagcg atggggcgg ggggggggg     420
ggggcgcgcg ccaggcgggg cggggcgggg cgaggggcgg ggcggggcga ggcggagagg    480
tgcggcggca gccaatcaga gcggcgcgct ccgaaagttt cctttatgg cgaggcggcg    540
gcggcggcgg ccctataaaa agcgaagcgc ggcgcgggcg ggagtcgctg cgacgctgcc    600
ttcgccccgt gccccgctcc gccgccgcct cgcgccgccc gccccggctc tgactgaccg    660
cgttactccc acaggtgagc gggcgggacg gcccttctcc tccgggctgt aattagctga    720
gcaagaggta agggtttaag ggatggttgg ttggtggggt attaatgttt aattacctgg    780
agcacctgcc tgaaatcact ttttttcagg ttggaccggt cgccaccatg gcgcaggagg    840
tggacactgc acagggggcc gagatgagaa aggagccgg agcagctaga ggacgggcca    900
gctggtgttg ggccttggcg ctgctctggc tggctgtggt gcctggctgg tccagagtgt    960
ccgggattcc ctcgaggcgc cattggcctg tgccatataa gcgcttcgac ttccggccta    1020
agcccgaccc gtactgccag gccaagtaca cctttgtcc caccggatcg cccatccctg     1080
tgatggaggc gacgatgac atcgaagtgt tccgactgca agccccgtg tgggaattca     1140
aatacggcga ccttctgggc cacctgaaga tcatgcatga cgccatcggg ttccgctcga    1200
ccctgaccgg aaagaactac accatggagt ggtacgaact gttccagctg ggaaactgca    1260
ccttccctca ccttcggcct gaaatggatg caccttctg gtgcaaccaa ggcgctgcct    1320
gcttctttga ggggatcgac gatgtgcact ggaaggagaa cggaaccctg gtccaagtgg   1380
ccactatctc cgggaacatg ttcaaccaga tggccaaatg ggtgaagcag gataatgaga   1440
ctggcatcta ctatgaaact tggaacgtga agccagccc ggagaagggt gccgaaacct   1500
ggttcgattc ctacgactgc tccaagttcg tgctgcggac cttcaacaag ctggccgagt    1560
tcggtgccga gttcaagaac attgaaacca actacactcg cattttcctc tactcgggcg    1620
aacccaccta cctgggaaac gaaactagcg tctttgggcc gactggaaac aagactttgg    1680
ggctcgcgat caagaggttc tactaccctt tcaagccgca ccttccgacc aaggaattct    1740
tgctgagcct gctgcagatt ttcgatgccg tgatcgtgca taagcagttc tatctgtttt    1800
acaatttcga atactggttc ctcccgatga agttcccgtt cattaagatc acctacgagg    1860
aaatcccact cccgatccgc aacaagaccc tgtccggtct gtaatagcgg ccgcgcggat    1920
ccctcgactg tgccttctag ttgccagcca tctgttgttt gccctcccc cgtgccttcc    1980
ttgaccctgg aaggtgccac tcccactgtc ctttcctaat aaaatgagga aattgcatcg    2040
cattgtctga gtaggtgtca ttctattctg ggggtgggg tgggcagga cagcaagggg    2100
gaggattggg aagacaacag caggcatgct ggggatgcgg tgggctctat ggcttctgag    2160
gcggaaagaa ccagct                                                     2176
```

<210> SEQ ID NO 11
<211> LENGTH: 2185
<212> TYPE: DNA
<213> ORGANISM: Artificial
<220> FEATURE:
<223> OTHER INFORMATION: Ovine CLN5 cassette

<400> SEQUENCE: 11

```
tacataactt acgtaaatg gcccgcctgg ctgaccgccc aacgacccc gcccattgac      60
gtcaataatg acgtatgttc ccatagtaac gccaataggg actttccatt gacgtcaatg    120
ggtggagtat ttacggtaaa ctgcccactt ggcagtacat caagtgtatc atatgccaag   180
tacgccccct attgacgtca atgacggtaa atggcccgcc tggcattatg cccagtacat   240
gaccttatgg gactttccta cttggcagta catctacgta ttagtcatcg ctattaccat   300
ggtcgaggtg agccccacgt tctgcttcac tctccccatc tccccccct ccccacccc    360
aattttgtat ttatttattt tttaattatt ttgtgcagcg atggggcgg gggggggggg   420
gggcgcgcg ccaggcgggg cggggcgggg cgaggggcgg ggcggggcga ggcggagagg   480
tgcggcggca gccaatcaga gcggcgcgct ccgaaagttt cctttatgg cgaggcggcg   540
gcggcggcgg ccctataaaa agcgaagcgc gcggcgggcg ggagtcgctg cgacgctgcc   600
ttcgccccgt gccccgctcc gccgccgcct cgcgccgccc gccccggctc tgactgaccg   660
cgttactccc acaggtgagc gggcgggacg gcccttctcc tccgggctgt aattagctga   720
gcaagaggta agggtttaag ggatggttgg ttggtggggt attaatgttt aattacctgg   780
agcacctgcc tgaaatcact tttttcagg ttggaccggt cgccaccatg cacaagcag    840
gaggagcagg ggcaggagct tgggaagga gaggagcagg agctggagcg ggccctgagc   900
gggccccttg gcgctgggcc ccggccctgc tgtggctcgc ggcggctact gccgctgccg   960
ccgccgccgg ggacccgtcc cggagacagt ggccggtgcc atacaagcgc ttcagctttc  1020
ggccccgagcc ggacccgtac tgtcaggcca agtacacctt ctgcccaacc ggctccccta 1080
tcccggtcat gaaggacgac gacgtcattg aagtgttcag gctccaagcc cccgtgtggg  1140
agttcaaata cggagatctg cttggtcact tgaagattat gcacgatgcg atcggctttc  1200
gctccaccct gaccgagaag aactacacta tggagtggta cgaattgttc cagctgggca  1260
actgcacttt ccccccacctg aggcccgaga tgaacgcgcc tttctggtgt aaccagggtg 1320
cagcctgctt tttcgagggc atcgacgaca accattggaa ggagaacggc accctggtcc  1380
tggtggccac aatcagcggc gggatgttca acaagatggc caaatgggtg aagcaggaca  1440
acgagactgg aatctattac gagacttgga ccgtgcaagc ctcacccaag aaggaggccg   1500
agaagtggtt cgagtcctac gactgctcaa agttcgtgct gcgcacctac gaaaagctgg   1560
ccgaacttgg agccgacttc aagaagatcg aaaccaacta cacccgcatc tttctgtatt  1620
cgggcgaacc cacgtacctg ggaaacgaaa cctccgtgtt cggccctacc gggaacaaga  1680
ctcttgctct cgccatcaag aagttctact acccgttcaa gccgcacctg tcgaccaagg   1740
aattcctcct gagcctgctg cagatctttg atgcggtggt cattcaccgg gaattctatc   1800
tgttctacaa tttcgagtac tggttcctcc ctatgaaatc cccattcatt aagatcactt    1860
acgaagaaat tccgctcccc aatcgcaaaa accggaccct gtccggtctg tgataacggc    1920
cgcgcggatc cctcgactgt gccttctagt tgccagccat ctgttgtttg cccctccccc    1980
gtgccttcct tgaccctgga aggtgccact cccactgtcc tttcctaata aaatgaggaa    2040
attgcatcgc attgtctgag taggtgtcat tctattctgg ggggtgggt ggggcaggac    2100
agcaagggg aggattggga agacaacagc aggcatgctg gggatgcggt gggctctatg    2160
gcttctgagg cggaaagaac cagct                                          2185
```

OPTIMIZED CLN5 GENES AND EXPRESSION CASSETTES AND THEIR USE

STATEMENT OF PRIORITY

This patent application is a 35 U.S.C. national phase application of PCT Application PCT/US2019/039458 filed Jun. 27, 2019, which claims the benefit, under 35 U.S.C. § 119(e), of U.S. Provisional Applications No. 62/691,359, filed on Jun. 28, 2018, and No. 62/828,717, filed on Apr. 3, 2019, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-853_ST25.txt, 14,513 bytes in size, generated on Dec. 17, 2020 and filed via EFS-Web, is provided in lieu of a paper copy. This Sequence Listing is hereby incorporated herein by reference into the specification for its disclosures.

FIELD OF THE INVENTION

This invention relates to polynucleotides comprising optimized CLN5 open reading frame (ORF) sequences, vectors comprising the same, and methods of using the same for delivery of the ORF to a cell or a subject and to treat disorders associated with aberrant expression of a CLN5 gene or aberrant activity of a CLN5 gene product in the subject, such as CLN5 disease.

BACKGROUND OF THE INVENTION

The neuronal ceroid lipofuscinoses (NCLs, "Batten disease") are neurodegenerative lysosomal storage diseases, predominantly affecting children. Batten disease are fatal and inherited, affecting the central nervous system (CNS) and caused by mutations in any of 13 different genes, designated CLN1-8 and 10-14. Despite their genetic diversity, the NCLs are defined by similar pathological and clinical features which include progressive neuronal loss, retinal degeneration, seizures and psychomotor decline culminating in premature death. Apart from a recently approved enzyme replacement therapy for the CLN2 disease (cerliponase alfa, BioMarin Pharmaceutical Inc.), there are no effective treatments, although several gene and enzyme replacement therapy trials are underway (NCT01161576, NCT01414985, NCT02485899, NCT02725580; clinicaltrials.gov) following studies in animal models (Sondhi et al., 2007 *Mol. Ther.* 15: 481-491; Sondhi et al., 2012 *Hum. Gene Ther. Methods* 23: 324-335; Palmer et al., 2015 *Acta-Mol. Basis Dis.* 1852: 2279-2286; Katz et al., 2014 *J. Neursci. Res.* 92: 1591-1598; Neverman et al., 2015 *Biochim. Biophys. Acta* 1852: 2292-2300).

Borderdale sheep can have naturally-occurring CLN5 Batten disease, caused by homozygous or compound heterozygous mutations in CLN5, an intracellular trafficking protein. Affected sheep share the main neuropathological features of the human disease, including progressive brain atrophy, loss of vision from 11-12 months of age, and typically decline to a humane endpoint before 22 months (Jolly et al., N. Z. Vet. J. 50: 199-202).

SUMMARY OF THE INVENTION

The present invention is based, in part, on the development of optimized CLN5 genes, expression cassettes, and vectors capable of providing therapeutic levels of CLN5 expression for treating disorders associated with CLN5 expression such as CLN5 disease.

Thus, one aspect of the invention relates to a polynucleotide comprising a human CLN5 open reading frame, wherein the human CLN5 open reading frame has been codon-optimized for expression in human cells.

A further aspect of the invention relates to an expression cassette comprising a polynucleotide comprising a human CLN5 open reading frame and vectors, transformed cells, and transgenic animals comprising the polynucleotide of the invention.

Another aspect of the invention relates to a pharmaceutical formulation comprising the polynucleotide, expression cassette, vector, and/or transformed cell of the invention in a pharmaceutically acceptable carrier.

An additional aspect of the invention relates to a method of expressing a CLN5 open reading frame in a cell, comprising contacting the cell with the polynucleotide, expression cassette, and/or vector of the invention, thereby expressing the CLN5 open reading frame in the cell.

A further aspect of the invention relates to a method of expressing a CLN5 open reading frame in a subject, comprising delivering to the subject the polynucleotide, expression cassette, vector, and/or transformed cell of the invention, thereby expressing the CLN5 open reading frame in the subject.

An additional aspect of the invention relates to a method of treating a disorder associated with aberrant expression of a CLN5 gene or aberrant activity of a CLN5 gene product in a subject in need thereof, comprising administering to the subject a therapeutically effective amount of the polynucleotide, expression cassette, vector, and/or transformed cell of the invention, such that the CLN5 open reading frame is expressed in the subject.

A further aspect of the invention relates to a method of treating CLN5 disease in a subject in need thereof, comprising administering to the subject a therapeutically effective amount of the polynucleotide, expression cassette, vector, and/or transformed cell of the invention, such that the CLN5 open reading frame is expressed in the subject.

Another aspect of the invention relates to a method of treating ceroid storage disease in a subject in need thereof, comprising administering to the subject a therapeutically effective amount of the polynucleotide, expression cassette, vector, and/or transformed cell of the invention, such that the CLN5 open reading frame is expressed in the subject.

An additional aspect of the invention relates to a method of treating Jansky-Bielschowsky disease in a subject in need thereof, comprising administering to the subject a therapeutically effective amount of the polynucleotide, expression cassette, vector, and/or transformed cell of the invention, such that the CLN5 open reading frame is expressed in the subject.

A further aspect of the invention relates to a method of treating variant late infantile neuronal ceroid lipofuscinosis (vLINCL) in a subject in need thereof, comprising administering to the subject a therapeutically effective amount of the polynucleotide, expression cassette, vector, and/or transformed cell of the invention, such that the CLN5 open reading frame is expressed in the subject.

Another aspect of the invention relates to a polynucleotide, expression cassette, vector, and/or transformed cell of the invention for use in a method of treating a disorder associated with aberrant expression of a CLN5 gene or aberrant activity of a CLN5 gene product in a subject in need thereof.

These and other aspects of the invention are set forth in more detail in the description of the invention below.

BRIEF DESCRIPTION OF THE DRAWINGS

FIG. 1A CLN5$^{-/-}$ sheep that received scAAV9-CLN5 gene therapy at a pre-clinical age (3 months (mo.)), an early clinical age (7 mo.) or more advanced clinical age (9 mo.) were assessed on the multimodal ovine Batten disease rating scale (oBDRS, Table 5) and compared against healthy CLN5$^{+/-}$ and untreated CLN5$^{-/-}$ controls over time. Lower scores reflect greater impairment. One of the 3-month and two of the 9-month treated sheep showed delayed disease onset but ultimately succumbed to the disease (data not shown). The onset of phenotypic disease traits were assessed including (FIG. 1B) absent menace response, (FIG. 1C) maze test failure, (FIG. 1D) ataxia, (FIG. 1E) tremors, (FIG. 1F) reduced mentation and (FIG. 1G) stereotypical behavior in the scAAV9 treated cohorts and untreated CLN5$^{-/-}$ sheep. Each point represents the age of onset for an individual sheep. Missing points indicate sheep did not yet exhibit the trait during the study. All data are expressed as means±SEM. *P<0.05, **P<0.01, nonparametric Mann-Whitney test where appropriate.

FIG. 2A shows a schematic of the maze. FIG. 2B shows mean traverse times for sheep treated pre-clinically (3 mo.), at an early clinical disease stage (7 mo.) or at a more advanced disease stage (9 mo.) with scAAV9-CLN5 compared with healthy CLN5$^{+/-}$ and untreated CLN5-controls (5 runs per animal at each time). All data are the means±SEM. The earliest time at which traverse times differed between cohorts are indicated. *P<0.05, Student's t-test.

FIGS. 8A-8B show electroretinography data demonstrating the decline in retinal function after brain-directed CLN5 gene therapy. FIG. 8A shows a representative electroretinogram for a CLN5$^{-/-}$ sheep, two years after receiving pre-clinical scAAV9-CLN5 gene therapy. Mixed receptor responses were plotted after 5 min. of dark adaptation. Amplitudes were reduced but resembled those of untreated 16 months CLN5$^{-/-}$ sheep. Note the normal electroretinography signal seen in the control CLN5$^{+/-}$ animal. FIG. 8B shows representative ERG traces over time for four CLN5$^{-/-}$ sheep who received scAAV9-CLN5 gene therapy at 7 months show the differential effect of treatment on retinal function.

DETAILED DESCRIPTION OF THE INVENTION

Figure 1A:
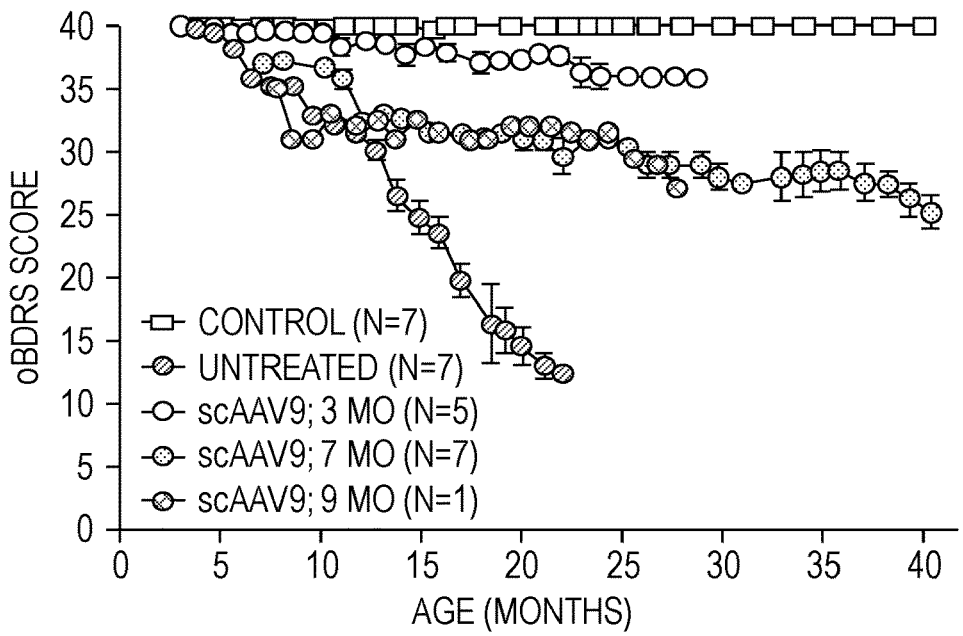
FIGS. 1A-1G shows that CLN5 gene therapy provides long-term clinical efficacy to CLN5 affected sheep.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) J. Virol. 78:6381-6388 and Table 1), which are also encompassed by the term "AAV."

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) Proc. Nat. Acad. Sci. USA 99:11854; Moris et al., (2004) Virol. 33-:375-383; Mori et al., (2004) Virol. 330: 375; Muramatsu et al., (1996) Virol. 221:208; Ruffing et al., (1994) J. Gen. Virol. 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of cells of the central nervous system (CNS) with only low transduction of peripheral organs (see e.g. U.S. Pat. No. 9,636,370 McCown et al., and US patent publication 2017/0360960 Gray et al.).

The term "disorder associated with aberrant expression of a CLN5 gene" as used herein refers to a disease, disorder, syndrome, or condition that is caused by or a symptom of decreased or altered expression of the CLN5 gene in a subject relative to the expression level in a normal subject or in a population.

TABLE 1

| AAV Serotypes/ Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |

TABLE 1-continued

| AAV Serotypes/Isolates | GenBank Accession Number |
|---|---|
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

The term "disorder associated with aberrant activity of a CLN5 gene product" as used herein refers to a disease, disorder, syndrome, or condition that is caused by or a symptom of decreased or altered activity of the CLN5 gene product in a subject relative to the activity in a normal subject or in a population.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide," "nucleic acid," or "nucleotide sequence" may be of RNA, DNA or DNA-RNA hybrid sequences (including both naturally occurring and non-naturally occurring nucleotides), but is preferably either a single or double stranded DNA sequence.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

The region in a nucleic acid sequence or polynucleotide in which one or more regulatory elements are found may be referred to as a "regulatory region."

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

The term "open reading frame (ORF)," as used herein, refers to the portion of a polynucleotide, e.g., a gene, that encodes a polypeptide. The term "coding region" may be used interchangeably with open reading frame.

The term "codon-optimized," as used herein, refers to a gene coding sequence that has been optimized to increase expression by substituting one or more codons normally present in a coding sequence (for example, in a wild-type sequence, including, e.g., a coding sequence for CLN5) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wild-type gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natd. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" (or grammatical equivalents) a virus vector, it is meant that the virus vector is at least partially separated from at least some of the other components in the starting material.

By the term "treat," "treating," or "treatment of" (or grammatically equivalent terms) is meant to reduce or to at least partially improve or ameliorate the severity of the subject's condition and/or to alleviate, mitigate or decrease in at least one clinical symptom and/or to delay the progression of the condition.

As used herein, the term "prevent," "prevents," or "prevention" (and grammatical equivalents thereof) means to delay or inhibit the onset of a disease. The terms are not meant to require complete abolition of disease, and encompass any type of prophylactic treatment to reduce the incidence of the condition or delays the onset of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid," with respect to a virus, is a sequence or nucleic acid, respectively, that is not naturally occurring in the virus. Generally, the heterologous nucleic acid or nucleotide sequence comprises an open reading frame that encodes a polypeptide and/or a nontranslated RNA.

A "vector" refers to a compound used as a vehicle to carry foreign genetic material into another cell, where it can be replicated and/or expressed. A cloning vector containing foreign nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs or expression cassettes) are for the expression of the exogenous gene in the target cell, and generally have a promoter sequence that drives expression of the exogenous gene/ORF. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a nanoparticle.

As used herein, the term "vector," "virus vector," "delivery vector" (and similar terms) in a specific embodiment generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (ITR) (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids, including non-naturally occurring amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |

TABLE 3-continued

Amino Acid Residue Derivatives

| Modified Amino Acid Residue | Abbreviation |
|---|---|
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) Annu. Rev. Biophys. Biomol. Struct. 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

CLN5 Expression Cassettes and Vectors

The present invention relates to the design of a CLN5 expression cassette to provide therapeutic levels of expression of CLN5 (also known as ceroid-lipofuscinosis neuronal protein 5), the enzyme encoded by the CLN5 gene, and the use of the expression cassette to achieve therapeutic levels of CLN5 in a subject.

Thus, one aspect of the invention relates to a polynucleotide comprising a mammalian CLN5 open reading frame (ORF), wherein the CLN5 open reading frame has been codon-optimized for expression in mammalian cells. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. The open reading frame is the portion of the CLN5 gene that encodes CLN5. In some embodiments, the mammalian CLN5 open reading frame may be a human or an ovine (i.e., sheep) CLN5 open reading frame. As used herein, a mammalian CLN5 ORF refers to a nucleotide sequence that encodes mammalian CLN5, e.g., a human or an ovine CLN5 ORF refers to a nucleotide sequence that encodes a human or an ovine CLN5. Codon optimization is a technique well known in the art and optimal codons for expression in different species are known. The use of a codon-optimized CLN5 sequence allows one to distinguish expression of the transduced sequence from expression of the endogenous CLN5 sequence in a subject.

In some embodiments, the codon-optimized CLN5 open reading frame encodes a CLN5 enzyme that is modified from the wild-type sequence, e.g., comprises, consists essentially of, or consists of an amino acid sequence in which 1, 2, 3, 4, or 5 residues have been substituted, added, and/or deleted compared to the wild-type amino acid sequence.

This invention is based, in part, on the novel discovery that the wildtype ovine CLN5 open reading frame start site (i.e., ATG initiation codon) corresponds to the third start site (i.e., ATG initiation codon) of the wildtype human CLN5 open reading frame, as opposed to the first and/or second start site of the human CLN5 open reading frame. Thus, the functional human CLN5 open reading frame begins at the third start site rather than the first and/or the second start site. Thus, in some embodiments, the codon-optimized human open reading frame starts from the third start site (i.e., ATG initiation codon) of the wildtype human CLN5.

In some embodiments, the codon-optimized CLN5 open reading frame comprises, consists essentially of, or consists of the nucleotide sequence of SEQ ID NO:1 or a sequence at least about 70% identical thereto, e.g., at least about 70, 75, 80, 85, 90, 91, 92, 93, 94, 95, 96, 97, 98, or 99% identical thereto.

```
Human codon-optimized CLN5 open reading frame
                                      SEQ ID NO: 1
ATGGCGCAGGAGGTGGACACTGCACAGGGGGCCGAGATGAGAAGAGGAG

CCGGAGCAGCTAGAGGACGGGCCAGCTGGTGTTGGGCCTTGGCGCTGCT

CTGGCTGGCTGTGGTGCCTGGCTGGTCCAGAGTGTCCGGGATTCCCTCG

AGGCGCCATTGGCCTGTGCCATATAAGCGCTTCGACTTCCGGCCTAAGC

CCGACCCGTACTGCCAGGCCAAGTACACCTTTTGTCCCACCGGATCGCC

CATCCCTGTGATGGAGGGCGACGATGACATCGAAGTGTTCCGACTGCAA

GCCCCCGTGTGGGAATTCAAATACGGCGACCTTCTGGGCCACCTGAAGA

TCATGCATGACGCCATCGGGTTCCGCTCGACCCTGACCGGAAAGAACTA

CACCATGGAGTGGTACGAACTGTTCCAGCTGGGAAACTGCACCTTCCCT

CACCTTCGGCCTGAAATGGATGCACCTTTCTGGTGCAACCAAGGCGCTG

CCTGCTTCTTTGAGGGGATCGACGATGTGCACTGGAAGGAGAACGGAAC

CCTGGTCCAAGTGGCCACTATCTCCGGGAACATGTTCAACCAGATGGCC

AAATGGGTGAAGCAGGATAATGAGACTGGCATCTACTATGAAACTTGGA

ACGTGAAAGCCAGCCCGGAGAAGGGTGCCGAAACCTGGTTCGATTCCTA

CGACTGCTCCAAGTTCGTGCTGCGGACCTTCAACAAGCTGGCCGAGTTC

GGTGCCGAGTTCAAGAACATTGAAACCAACTACACTCGCATTTTCCTCT

ACTCGGGCGAACCCACCTACCTGGGAAACGAAACTAGCGTCTTTGGGCC

GACTGGAAACAAGACTTTGGGGCTCGCGATCAAGAGGTTCTACTACCCT

TTCAAGCCGCACCTTCCGACCAAGGAATTCTTGCTGAGCCTGCTGCAGA

TTTTCGATGCCGTGATCGTGCATAAGCAGTTCTATCTGTTTTACAATTT
```

In some embodiments, the codon-optimized CLN5 open reading frame comprises, consists essentially of, or consists of the nucleotide sequence of SEQ ID NO:2 or a sequence at least about 70% identical thereto, e.g., at least about 70, 75, 80, 85, 90, 91, 92, 93, 94, 95, 96, 97, 98, or 99% identical thereto.

```
Ovine codon-optimized CLN5 open reading frame
                                        SEQ ID NO: 2
ATGGCACAAGCAGGAGGAGCAGGGGCAGGAGCTTGGGGAAGGAGAGGAG

CAGGAGCTGGAGCGGGCCCTGAGCGGGCCCCTTGGCGCTGGGCCCCGGC

CCTGCTGTGGCTCGCGGCGGCTACTGCCGCTGCCGCCGCCGCCGGGGAC

CCGTCCCGGAGACAGTGGCCGGTGCCATACAAGCGCTTCAGCTTTCGGC

CCGAGCCGGACCCGTACTGTCAGGCCAAGTACACCTTCTGCCCAACCGG

CTCCCCTATCCCGGTCATGAAGGACGACGACGTCATTGAAGTGTTCAGG

CTCCAAGCCCCGTGTGGGAGTTCAAATACGGAGATCTGCTTGGTCACT

TGAAGATTATGCACGATGCGATCGGCTTTCGCTCCACCCTGACCGAGAA

GAACTACACTATGGAGTGGTACGAATTGTTCCAGCTGGGCAACTGCACT

TTCCCCCACCTGAGGCCCGAGATGAACGCGCCTTTCTGGTGTAACCAGG

GTGCAGCCTGCTTTTTCGAGGGCATCGACGACAACCATTGGAAGGAGAA

CGGCACCCTGGTCCTGGTGGCCACAATCAGCGGCGGGATGTTCAACAAG

ATGGCCAAATGGGTGAAGCAGGACAACGAGACTGGAATCTATTACGAGA

CTTGGACCGTGCAAGCCTCACCCAAGAAGGAGGCCGAGAAGTGGTTCGA

GTCCTACGACTGCTCAAAGTTCGTGCTGCGCACCTACGAAAAGCTGGCC

GAACTTGGAGCCGACTTCAAGAAGATCGAAACCAACTACACCCGCATCT

TTCTGTATTCGGGCGAACCCACGTACCTGGGAAACGAAACCTCCGTGTT

CGGCCCTACCGGGAACAAGACTCTTGCTCTCGCCATCAAGAAGTTCTAC

TACCCGTTCAAGCCGCACCTGTCGACCAAGGAATTCCTCCTGAGCCTGC

TGCAGATCTTTGATGCGGTGGTCATTCACCGGGAATTCTATCTGTTCTA

CAATTTCGAGTACTGGTTCCTCCCTATGAAATCCCCATTCATTAAGATC

ACTTACGAAGAAATTCCGCTCCCCAATCGCAAAAACCGGACCCTGTCCG

GTCTGTGATAA
```

Another aspect of the invention relates to an expression cassette comprising a polynucleotide comprising a human or an ovine CLN5 open reading frame. In certain embodiments, the polynucleotide is a human or an ovine codon-optimized sequence, e.g., a polynucleotide comprising the nucleotide sequence of SEQ ID NO:1 or SEQ ID NO:2, or a sequence at least about 70% identical thereto, e.g., at least about 70, 75, 80, 85, 90, 91, 92, 93, 94, 95, 96, 97, 98, or 99% identical thereto.

The CLN5 open reading frame in the expression cassette may be operably linked to one or more expression elements that may enhance expression of CLN5. In some embodiments, the polynucleotide is operably linked to a promoter, e.g., a chicken beta-actin promoter, e.g., a promoter comprising, consisting essentially of, or consisting of the nucleotide sequence of SEQ ID NO:3 or a sequence at least about 70% identical thereto, e.g., at least about 70, 75, 80, 85, 90, 91, 92, 93, 94, 95, 96, 97, 98, or 99% identical thereto. In some embodiments, the promoter further comprises the chimeric intron with chicken beta-actin splicing donor site and minute virus of mice (MVM) intron splicing acceptor site, e.g., comprising, consisting essentially of, or consisting of the nucleotide sequence of SEQ ID NO:4 or a sequence at least about 70% identical thereto, e.g., at least about 70, 75, 80, 85, 90, 91, 92, 93, 94, 95, 96, 97, 98, or 99% identical thereto.

```
Chicken beta-actin promoter
                                        SEQ ID NO: 3
TACGTATTAGTCATCGCTATTACCATGGTCGAGGTGAGCCCCACGTTCT

GCTTCACTCTCCCCATCTCCCCCCCCTCCCCACCCCCAATTTTGTATTT

ATTTATTTTTTAATTATTTTGTGCAGCGATGGGGGCGGGGGGGGGGGG

GGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTT

TCCTTTTATGGCGAGGCGGCGGCGGCGGCGGCCCTATAAAAAGCGAAGC

GCGCGGCGGGCG

Chimeric intron with chicken beta-actin splicing
donor site and minute virus of mice (MVM) intron
splicing acceptor site
                                        SEQ ID NO: 4
GGAGTCGCTGCGACGCTGCCTTCGCCCCGTGCCCCGCTCCGCCGCCGCC

TCGCGCCGCCCGCCCCGGCTCTGACTGACCGCGTTACTCCCACAGGTGA

GCGGGCGGGACGGCCCTTCTCCTCCGGGCTGTAATTAGC
```

In some embodiments, the polynucleotide is operably linked to a promoter, e.g., a CAGGS promoter, e.g., a promoter comprising, consisting essentially of, or consisting of the nucleotide sequence of SEQ ID NO:5 or a sequence at least about 70% identical thereto, e.g., at least about 70, 75, 80, 85, 90, 91, 92, 93, 94, 95, 96, 97, 98, or 99% identical thereto.

```
CAGGS promoter 1.6kb CMV enhancer, CBA promoter
and partial 5' UTR
                                        SEQ ID NO: 5
GATCTGAATTCGGATCTTCAATATTGGCCATTAGCCATATTATTCATTG

GTTATATAGCATAAATCAATATTGGATATTGGCCATTGCATACGTTGTA

TCTATATCATAATATGTACATTTATATTGGCTCATGTCCAATATGACCG

CCATGTTGGCATTGATTATTGACTAGTTATTAATAGTAATCAATTACGG

GGTCATTAGTTCATAGCCCATATATGGAGTTCCGCGTTACATAACTTAC

GGTAAATGGCCCGCCTGGCTGACCGCCCAACGACCCCCGCCCATTGACG

TCAATAATGACGTATGTTCCCATAGTAACGCCAATAGGGACTTTCCATT

GACGTCAATGGGTGGAGTATTTACGGTAAACTGCCCACTTGGCAGTACA

TCAAGTGTATCATATGCCAAGTCCGCCCCCTATTGACGTCAATGACGGT

AAATGGCCCGCCTGGCATTATGCCCAGTACATGACCTTACGGGACTTTC

CTACTTGGCAGTACATCTACGTATTAGTCATCGCTATTACCATGGTCGA

GGTGAGCCCCACGTTCTGCTTCACTCTCCCCATCTCCCCCCCCTCCCCA

CCCCCAATTTTGTATTTATTTATTTTTTAATTATTTTGTGCAGCGATGG

GGGCGGGGGGGGGGGGGGGCGCGCGCCAGGCGGGGCGGGGCGGGGCGA
```

-continued

```
GGGGGGGGGCGGGGCGAGGCGGAGAGGTGCGGCGGCAGCCAATCAGAGC

GGCGCGCTCCGAAAGTTTCCTTTTATGGCGAGGCGGCGGCGGCGGCGGC

CCTATAAAAGCGAAGCGCGCGGCGGGCGGGAGTCGCTGCGACGCTGCC

TTCGCCCCGTGCCCCGCTCCGCCGCCGCCTCGCGCCGCCCGCCCCGGCT

CTGACTGACCGCGTTACTCCCACAGGTGAGCGGGCGGGACGGCCCTTCT

CCTCCGGGCTGTAATTAGCGCTTGGTTTAATGACGGCTTGTTTCTTTTC

TGTGGCTGCGTGAAAGCCTTGAGGGGCTCCGGGAGGGCCCTTTGTGCGG

GGGGGAGCGGCTCGGGGGGTGCGTGCGTGTGTGTGCGTGGGGAGCGC

CGCGTGCGGCCCGCGCTGCCCGGCGGCTGTGAGCGCTGCGGGCGCGGCG

CGGGGCTTTGTGCGCTCCGCAGTGTGCGCGAGGGGAGCGCGGCCGGGGG

CGGTGCCCCGCGGTGCGGGGGGGCTGCGAGGGGAACAAAGGCTGCGTG

CGGGGTGTGTGCGTGGGGGGGTGAGCAGGGGGTATGGGCGCGGCGGTCG

GGCTGTAACCCCCCCCTGCACCCCCCTCCCCGAGTTGCTGAGCACGGCC

CGGCTTCGGGTGCGGGGCTCCGTACGGGGCGTGGCGCGGGGCTCGCCGT

GCCGGGCGGGGGTGGCGGCAGGTGGGGGTGCCGGCGGGGCGGGGCCG

CCTCGGGCCGGGGAGGGCTCGGGGGAGGGGCGCGGCGGCCCCCGGAGCG

CCGGCGGCTGTCGAGGCGCGGCGAGCCGCAGCCATTGCCTTTTATGGTA

ATCGTGCGAGAGGGCGCAGGGACTTACTTTGTCCCAAATCTGTGCGGAG

CCGAAATCTGGGAGGCGCCGCCGCACCCCCTCTAGCGGGCGCGGGGCGA

AGCGGTGCGGCGCCGGCAGGAAGGAAATGGGCGGGAGGGCCTTCGTGC

GTCGCCGCGCCGCCGTCCCCTTCTCCCTCTCCAGCCTCGGGGCTGTCCG

CGGGGGGACGGCTGCCTTCGGGGGGGACGGGGCAGGGCGGGGTTCGGCT

TCTGGCGTGTGACCGGCGGCTCTAGAGCCTCTGCTAACCATGTTCATGC

CTTCTTCTTTTTCCTACAGCTCCTGGGCAACGTGCTGGTTATTGTGCTG

TCTCATCATTTTGGCAAAG
```

In some embodiments, the polynucleotide is operably linked to an enhancer, e.g., a cytomegalovirus (CMV) enhancer, e.g., an enhancer comprising, consisting essentially of, or consisting of the nucleotide sequence of SEQ ID NO:6 or a sequence at least about 70% identical thereto, e.g., at least about 70, 75, 80, 85, 90, 91, 92, 93, 94, 95, 96, 97, 98, or 99% identical thereto.

CMV enhancer
SEQ ID NO: 6
```
TACATAACTTACGGTAAATGGCCCGCCTGGCTGACCGCCCAACGACCCC

CGCCCATTGACGTCAATAGTAACGCCAATAGGGACTTTCCATTGACGTC

AATGGGTGGAGTATTTACGGTAAACTGCCCACTTGGCAGTACATCAAGT

GTATCATATGCCAAGTACGCCCCCTATTGACGTCAATGACGGTAAATGG

CCCGCCTGGCATTGTGCCCAGTACATGACCTTATGGGACTTTCCTACTT

GGCAGTACATC
```

In some embodiments, the CLN5 open reading frame is operably linked to a polyadenylation signal, e.g., a synthetic polyadenylation signal, e.g., a polyadenylation signal comprising, consisting essentially of, or consisting of the nucleotide sequence of SEQ ID NO:7 or a sequence at least about 70% identical thereto, e.g., at least about 70, 75, 80, 85, 90, 91, 92, 93, 94, 95, 96, 97, 98, or 99% identical thereto. In some embodiments, the CLN5 open reading frame is operably linked to a polyadenylation signal, e.g., a simian virus 40 (SV40) polyadenylation signal, e.g., a polyadenylation signal comprising, consisting essentially of, or consisting of the nucleotide sequence of SEQ ID NO:8 or a sequence at least about 70% identical thereto, e.g., at least about 70, 75, 80, 85, 90, 91, 92, 93, 94, 95, 96, 97, 98, or 99% identical thereto. In some embodiments, the CLN5 open reading frame is operably linked to a polyadenylation signal, e.g., a bovine growth hormone (BGH) polyadenylation signal, e.g., a polyadenylation signal comprising, consisting essentially of, or consisting of the nucleotide sequence of SEQ ID NO:9 or a sequence at least about 70% identical thereto, e.g., at least about 70, 75, 80, 85, 90, 91, 92, 93, 94, 95, 96, 97, 98, or 99% identical thereto.

Synthetic polyadenylation signal (SpA)
SEQ ID NO: 7
```
AATAAAGAGCTCAGATGCATCGATCAGAGTGTGTTGGTTTTTTGTGTG
```

SV40 polyadenylation signal (SV40pA)
SEQ ID NO: 8
```
AGACATGATAAGATACATTGATGAGTTTGGACAAACCACAACTAGAATG

CAGTGAAAAAAATGCTTTATTTGTGAAATTTGTGATGCTATTGCTTTAT

TTGTAACCATTATAAGCTGCAATAAACAAGTTAACAACAACAATT
``` ovine growth hormone polyadenylation signal (BGHpA)
SEQ ID NO: 9
```
CTCGACTGTGCCTTCTAGTTGCCAGCCATCTGTTGTTTGCCCCTCCCCC

GTGCCTTCCTTGACCCTGGAAGGTGCCACTCCCACTGTCCTTTCCTAAT

AAAATGAGGAAATTGCATCGCATTGTCTGAGTAGGTGTCATTCTATTCT

GGGGGGTGGGGTGGGGCAGGACAGCAAGGGGGAGGATTGGGAAGACAAC

AGCAGGCATGCTGGGGATGCGGTGGGCTCTATGGCTTCTGAGGCGGAAA

GAACCAGCT
```

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancers elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the CLN5 open reading frame is transcribed and then translated in the target cells, specific initiation signals are generally employed for efficient translation of inserted protein coding sequences. These exogenous translational control sequences, which may include the ATG initiation codon (i.e., translation start site) and adjacent sequences, can be of a variety of origins, both natural and synthetic.

In certain embodiments, the expression cassette further comprises at least one adeno-associated virus (AAV) inverted terminal repeat (ITR), e.g., two AAV ITRs. The two ITRs may have the same nucleotide sequence or different nucleotide sequences. The AAV ITRs may be from any AAV serotype, e.g., AAV2. Each ITR independently may be the wild-type sequence or a modified sequence. In some embodiments, a modified ITR may have a D-element deletion (WO 01/92551). A D-element deletion is defined as the removal of that portion of the ITR known as the D-element. The D-element can be alternatively referred to or known as a D region, or D sequence, and/or the nucleotides of the ITR that do not form palindromic hairpin structures. In some embodiments, the expression cassette is an AAV genome, e.g., a self-complementary AAV genome.

In certain embodiments, the expression cassette comprises an enhancer, a promoter, a human or an ovine CLN5 open reading frame, and a polyadenylation site, optionally in the recited order. In certain embodiments, the expression cassette comprises an AAV ITR, an enhancer, a promoter, a human or an ovine CLN5 open reading frame, a polyadenylation site, and an AAV ITR, optionally in the recited order. In certain embodiments, the expression cassette comprises a CMV enhancer, a chicken beta actin promoter, a human or an ovine CLN5 open reading frame, and a BGHpA polyadenylation site, optionally in the recited order. In certain embodiments, the expression cassette comprises an AAV ITR, a CMV enhancer, a chicken beta actin promoter, a human or an ovine CLN5 open reading frame, a BGHpA polyadenylation site, and an AAV ITR, optionally in the recited order. In certain embodiments, the expression cassette comprises an AAV2 ITR, a CMV enhancer, a chicken beta actin promoter, a human CLN5 open reading frame, a BGHpA polyadenylation site, and an AA2V ITR, optionally in the recited order. In certain embodiments, the expression cassette comprises an AAV2 ITR, a CMV enhancer, a chicken beta actin promoter, an ovine CLN5 open reading frame, a BGHpA polyadenylation site, and an AA2V ITR, optionally in the recited order. The aforementioned components are in operable linkage.

In some embodiments, the expression cassette comprise, consists essentially of, or consists of the nucleotide sequence of SEQ ID NO:10 or a sequence at least about 70% identical thereto, e.g., at least about 70, 75, 80, 85, 90, 91, 92, 93, 94, 95, 96, 97, 98, or 99% identical thereto.

Human CLN5 expression cassette not including ITRs
SEQ ID NO: 10

```
tacataacttacggtaaatggcccgcctggctgaccgcccaacgacccc
cgcccattgacgtcaataatgacgtatgttcccatagtaacgccaatag
ggactttccattgacgtcaatgggtggagtatttacggtaaactgccca
cttggcagtacatcaagtgtatcatatgccaagtacgcccoctattgac
gtcaatgacggtaaatggcccgcctggcattatgcccagtacatgacct
tatgggactttcctacttggcagtacatctacgtattagtcatcgctat
taccatggtcgaggtgagccccacgttctgcttcactctccccatctcc
ccccctccccaccccaatttttgtatttatttattttttaattatttt
gtgcagcgatgggggcggggggggggggggcgcgcgccaggcggggg
gggcggggcgaggggggggcggggcgaggcggagaggtgcggcggcagc
caatcagagcggcgcgctccgaaagtttccttttatggcgaggcggcgg
cggcggcggccctataaaaagcgaagcgcgcggggggggagtcgctgcg
acgctgccttcgccccgtgccccgctccgccgccgcctcgcgccgcccg
ccccggctctgactgaccgcgttactcccacaggtgagcgggcgggacg
gcccttctcctccgggctgtaattagctgagcaagaggtaagggtttaa
gggatggttggttggtggggtattaatgtttaattacctggagcacctg
cctgaaatcactttttttcaggttggaccggtcgccaccATGGCGCAGG
AGGTGGACACTGCACAGGGGGCCGAGATGAGAAGAGGAGCCGGAGCAGC
TAGAGGACGGGCCAGCTGGTGTTGGGCCTTGGCGCTGCTCTGGCTGGCT
GTGGTGCCTGGCTGGTCCAGAGTGTCCGGGATTCCCTCGAGGCGCCATT
GGCCTGTGCCATATAAGCGCTTCGACTTCCGGCCTAAGCCCGACCCGTA
CTGCCAGGCCAAGTACACCTTTTGTCCCACCGGATCGCCCATCCCTGTG
ATGGAGGGCGACGATGACATCGAAGTGTTCCGACTGCAAGCCCCCGTGT
GGGAATTCAAATACGGCGACCTTCTGGGCCACCTGAAGATCATGCATGA
CGCCATCGGGTTCCGCTCGACCCTGACCGGAAAGAACTACACCATGGAG
TGGTACGAACTGTTCCAGCTGGGAAACTGCACCTTCCCTCACCTTCGGC
CTGAAATGGATGCACCTTTCTGGTGCAACCAAGGCGCTGCCTGCTTCTT
TGAGGGGATCGACGATGTGCACTGGAAGGAGAACGGAACCCTGGTCCAA
GTGGCCACTATCTCCGGGAACATGTTCAACCAGATGGCCAAATGGGTGA
AGCAGGATAATGAGACTGGCATCTACTATGAAACTTGGAACGTGAAAGC
CAGCCCGGAGAAGGGTGCCGAAACCTGGTTCGATTCCTACGACTGCTCC
AAGTTCGTGCTGCGGACCTTCAACAAGCTGGCCGAGTTCGGTGCCGAGT
TCAAGAACATTGAAACCAACTACACTCGCATTTTCCTCTACTCGGGCGA
ACCCACCTACCTGGGAAACGAAACTAGCGTCTTTGGGCCGACTGGAAAC
AAGACTTTGGGGCTCGCGATCAAGAGGTTCTACTACCCTTTCAAGCCGC
ACCTTCCGACCAAGGAATTCTTGCTGAGCCTGCTGCAGATTTTCGATGC
CGTGATCGTGCATAAGCAGTTCTATCTGTTTTACAATTTCGAATACTGG
TTCCTCCCGATGAAGTTCCCGTTCATTAAGATCACCTACGAGGAAATCC
CACTCCCGATCCGCAACAAGACCCTGTCCGGTCTGTAAtagcggccgcg
cggatccctcgactgtgccttctagttgccagccatctgttgtttgccc
```

-continued ctccccgtgccttccttgaccctggaaggtgccactcccactgtcctt tcctaataaaatgaggaaattgcatcgcattgtctgagtaggtgtcatt ctattctggggggtggggtggggcaggacagcaaggggaggattggga agacaacagcaggcatgctggggatgcggtgggctctatggcttctgag gcggaaagaaccagct In some embodiments, the expression cassette comprise, consists essentially of, or consists of the nucleotide sequence of SEQ ID NO:11 or a sequence at least about 70% identical thereto, e.g., at least about 70, 75, 80, 85, 90, 91, 92, 93, 94, 95, 96, 97, 98, or 99% identical thereto.

Ovine CLN5 expression cassette not including ITRs
SEQ ID NO: 11
tacataacttacggtaaatggcccgcctggctgaccgcccaacgacccc cgcccattgacgtcaataatgacgtatgttcccatagtaacgccaatag ggactttccattgacgtcaatgggtggagtatttacggtaaactgccca cttggcagtacatcaagtgtatcatatgccaagtacgcccctattgac gtcaatgacggtaaatggcccgcctggcattatgcccagtacatgacct tatgggactttcctacttggcagtacatctacgtattagtcatcgctat taccatggtcgaggtgagcccacgttctgcttcactctcccatctcc cccccctccccaccccaatttgtatttattatttttttaattattttt gtgcagcgatgggggcgggggggggggggggcgcgcgccaggcggggc ggggcggggcgaggggcgggggggcgaggcggagaggtgcggcggcag ccaatcagagcggcgcgctccgaaagtttccttttatggcgaggcggcg gcggcggcggccctataaaaagcgaagcgcgcggggggggagtcgctgc gacgctgccttcgcccgtgccccgctccgccgccgcctcgcgccgccc gccccggctctgactgaccgcgttactcccacaggtgagcgggggacg gcccttctcctccgggctgtaattagctgagcaagaggtaagggtttaa gggatggttggttggtggggtattaatgtttaattacctggagcacctg cctgaaatcacttttttcaggttggaccggtcgccaccATGGCACAAG

CAGGAGGAGCAGGGGCAGGAGCTTGGGGAAGGAGAGGAGCAGGAGCTGG

AGCGGGCCCTGAGCGGGCCCCTTGGCGCTGGGCCCCGGCCCTGCTGTGG

CTCGCGGCGGCTACTGCCGCTGCCGCCGCCGCCGGGGACCCGTCCCGGA

GACAGTGGCCGGTGCCATACAAGCGCTTCAGCTTTCGGCCCGAGCCGGA

CCCGTACTGTCAGGCCAAGTACACCTTCTGCCCAACCGGCTCCCCTATC

CCGGTCATGAAGGACGACGACGTCATTGAAGTGTTCAGGCTCCAAGCCC

CCGTGTGGGAGTTCAAATACGGAGATCTGCTTGGTCACTTGAAGATTAT

GCACGATGCGATCGGCTTTCGCTCCACCCTGACCGAGAAGAACTACACT

ATGGAGTGGTACGAATTGTTCCAGCTGGGCAACTGCACTTTCCCCCACC

TGAGGCCCGAGATGAACGCGCCTTTCTGGTGTAACCAGGGTGCAGCCTG

CTTTTTCGAGGGCATCGACGACAACCATTGGAAGGAGAACGGCACCCTG

GTCCTGGTGGCCACAATCAGCGGCGGGATGTTCAACAAGATGGCCAAAT

GGGTGAAGCAGGACAACGAGACTGGAATCTATTACGAGACTTGGACCGT

GCAAGCCTCACCCAAGAAGGAGGCCGAGAAGTGGTTCGAGTCCTACGAC

TGCTCAAAGTTCGTGCTGCGCACCTACGAAAAGCTGGCCGAACTTGGAG

CCGACTTCAAGAAGATCGAAACCAACTACACCCGCATCTTTCTGTATTC

GGGCGAACCCACGTACCTGGGAAACGAAACCTCCGTGTTCGGCCCTACC

GGGAACAAGACTCTTGCTCTCGCCATCAAGAAGTTCTACTACCCGTTCA

AGCCGCACCTGTCGACCAAGGAATTCCTCCTGAGCCTGCTGCAGATCTT

TGATGCGGTGGTCATTCACCGGGAATTCTATCTGTTCTACAATTTCGAG

TACTGGTTCCTCCCTATGAAATCCCCATTCATTAAGATCACTTACGAAG

AAATTCCGCTCCCCAATCGCAAAAACCGGACCCTGTCCGGTCTGTGATA

Acggccgcgcggatccctcgactgtgccttctagttgccagccatctgt tgtttgcccctccccgtgccttccttgaccctggaaggtgccactccc actgtcctttcctaataaaatgaggaaattgcatcgcattgtctgagta ggtgtcattctattctggggggtggggtggggcaggacagcaaggggga ggattgggaagacaacagcaggcatgctggggatgcggtgggctctatg gcttctgaggcggaaagaaccagct A further aspect of the invention relates to a vector comprising the polynucleotide or the expression cassette of the invention. Suitable vectors include, but are not limited to, a plasmid, phage, viral vector (e.g., an AAV vector, a lentiviral vector, an adenovirus vector, a herpesvirus vector, an alphavirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a delivery vehicle such as a particle (e.g., a microparticle or nanoparticle) or a liposome to which the expression cassette is attached or in which the expression cassette is embedded. The vector may be any delivery vehicle suitable to carry the expression cassette into a cell.

In some embodiments, the vector is a viral vector, e.g., a lentiviral vector and/or an AAV vector. The AAV vector may be any AAV serotype, e.g., AAV9. In some embodiments, the AAV vector may comprise wild-type capsid proteins. In other embodiments, the AAV vector may comprise a modified capsid protein with altered tropism compared to a wild-type capsid protein, e.g., a modified capsid protein is liver-detargeted or has enhanced tropism for particular cells.

In some embodiments, the vector is a single-stranded AAV (ssAAV) vector. In some embodiments, the vector is a self-complementary or duplexed AAV (scAAV) vector. scAAV vectors are described in international patent publication WO 01/92551 (the disclosure of which is incorporated herein by reference in its entirety). Use of scAAV to express the CLN5 ORF may provide an increase in the number of cells transduced, the copy number per transduced cell, or both.

An additional aspect of the invention relates to a transformed cell comprising the polynucleotide, expression cassette, and/or vector of the invention. In some embodiments, the polynucleotide, expression cassette, and/or vector is stably incorporated into the cell genome. The cell may be an in vitro, ex vivo, or in vivo cell.

Another aspect of the invention relates to a transgenic animal comprising the polynucleotide, expression cassette, vector, and/or the transformed cell of the invention. In some embodiments, the animal is a laboratory animal, e.g., a mouse, rat, rabbit, dog, monkey, or non-human primate.

A further aspect of the invention relates to a pharmaceutical formulation comprising the polynucleotide, expression cassette, vector, and/or transformed cell of the invention in a pharmaceutically acceptable carrier.

In a specific embodiment, the polynucleotide, expression cassette, vector, and/or transformed cell of the invention is isolated.

In another specific embodiment, the polynucleotide, expression cassette, vector, and/or transformed cell of the invention is purified.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a sheep, primate, or human cell). As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158: 67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by an AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377).

As a further alternative, the virus vectors of the invention can be produced in insect cells using baculovirus vectors to deliver the rep/cap genes and AAV template as described, for example, by Urabe et al., (2002) *Human Gene Ther.* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Methods of Using CLN5 Vectors

The present invention also relates to methods for delivering a CLN5 ORF to a cell or a subject to increase production of CLN5, e.g., for therapeutic or research purposes in vitro, ex vivo, or in vivo. Thus, one aspect of the invention relates to a method of expressing a CLN5 open reading frame in a cell, comprising contacting the cell with the polynucleotide, expression cassette, and/or the vector of the invention, thereby expressing the CLN5 open reading frame in the cell. In some embodiments, the cell is an in vitro cell, an ex vivo cell, or an in vivo cell.

Another aspect of the invention relates to a method of expressing a CLN5 open reading frame in a subject, comprising delivering to the subject the polynucleotide, expression cassette, vector, and/or transformed cell of the invention, thereby expressing the CLN5 open reading frame in the subject. In some embodiments, the subject is an animal model of a disorder associated with aberrant CLN5 gene expression. In some embodiments, the animal model of a disorder associated with aberrant CLN5 gene expression is a sheep.

A further aspect of the invention relates to a method of treating a disorder associated with aberrant expression of a CLN5 gene or aberrant activity of a CLN5 gene product in a subject in need thereof, comprising delivering to the subject a therapeutically effective amount of the polynucleotide, expression cassette, vector, and/or transformed cell of the invention, thereby treating the disorder associated with aberrant expression of the CLN5 gene or aberrant activity of a CLN5 gene product in the subject. The invention provides a method of treating a disorder associated with aberrant expression of a CLN5 gene or aberrant activity of a CLN5 gene product in a subject in need thereof, comprising administering to the subject a therapeutically effective amount of the polynucleotide, the expression cassette, vector, and/or transformed cell of the invention, such that the CLN5 open reading frame is expressed in the subject. In some embodiments, the disorder associated with expression of the CLN5 gene or gene product may be CLN5 disease. In some embodiments, the disorder associated with expression of the CLN5 gene or gene product may be a ceroid storage disease. In some embodiments, the disorder associated with expression of the CLN5 gene or gene product may be a neuronal ceroid lipofuscinosis (NCL) disease, also known as Batten disease. In some embodiments, a NCL disease may be variant late infantile NCL (vLINCL), referred to interchangeably as "Finnish" vLINCL. In some embodiments, the disorder associated with expression of the CLN5 gene or gene product may be Jansky-Bielschowsky disease.

The invention further provides a method of treating CLN5 disease in a subject in need thereof, comprising administering to the subject a therapeutically effective amount of the polynucleotide, the expression cassette, vector, and/or transformed cell of the invention, such that the CLN5 open reading frame is expressed in the subject.

The invention further provides a method of treating ceroid storage disease in a subject in need thereof, comprising administering to the subject a therapeutically effective amount of the polynucleotide, the expression cassette, vector, and/or transformed cell of the invention, such that the CLN5 open reading frame is expressed in the subject.

The invention further provides a method of treating Jansky-Bielschowsky disease in a subject in need thereof, comprising administering to the subject a therapeutically effective amount of the polynucleotide, the expression cassette, vector, and/or transformed cell of the invention, such that the CLN5 open reading frame is expressed in the subject.

The invention further provides a method of treating vLINCL disease in a subject in need thereof, comprising administering to the subject a therapeutically effective amount of the polynucleotide, the expression cassette, vector, and/or transformed cell of the invention, such that the CLN5 open reading frame is expressed in the subject.

In some embodiments, the methods of the present invention further comprise administering to the subject a bone marrow transplant (BMT), e.g., prior to administering the effective amount of a polynucleotide, expression cassette, vector, and/or transformed cell of the present invention. Techniques for performing BMT (referred to interchangeably as a hematopoietic stem cell transplant (HSCT)) are well known to those of skill in the art, and are routine for clinicians in the treatment of subjects (e.g., patients, e.g., sheep and/or human patients) in need thereof. The skilled clinician can readily determine the proper regimen to be used for performing BMT based on factors including the age and condition of the subject, type of disease being treated, stage of the disease, patient size, and the like.

In certain embodiments, the polynucleotide, expression cassette, vector, and/or transformed cell is delivered to the subject, e.g., systemically (e.g., intravenously) or directly to the central nervous system (e.g., to the cerebrospinal fluid by intrathecal or intraventricular injection) of the subject. In some embodiments, the polynucleotide, expression cassette, vector, and/or transformed cell is delivered intravenously. In some embodiments, the polynucleotide, expression cassette, vector, and/or transformed cell is delivered intracerebroventricularly.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease. Preferably, the subject is a human. In some embodiments, the subject is a sheep.

In certain embodiments, the polynucleotide of the invention is administered to a subject in need thereof as early as possible in the life of the subject, e.g., as soon as the subject is diagnosed with aberrant CLN5 expression or activity or any of the above-mentioned diseases or disorders. In some embodiments, the polynucleotide is administered to a newborn subject, e.g., after newborn screening has identified aberrant CLN5 expression or activity. In some embodiments, the polynucleotide is administered to a fetus in utero, e.g., after prenatal screening has identified aberrant CLN5 expression or activity or the presence of one of the above-mentioned diseases or disorders. In some embodiments, the polynucleotide is administered to a subject as soon as the subject develops symptoms associated with aberrant CLN5 expression or activity or is suspected or diagnosed as having aberrant CLN5 expression or activity or one of the above-mentioned diseases or disorders. In some embodiments, the polynucleotide is administered to a subject before the subject develops symptoms associated with aberrant CLN5 expression or activity or disease/disorder, e.g., a subject that is suspected or diagnosed as having aberrant CLN5 expression or activity or one of the above-mentioned diseases or disorders but has not started to exhibit symptoms.

In particular embodiments, the present invention provides a pharmaceutical composition comprising a polynucleotide, expression cassette, vector, and/or transformed cell of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a CLN5 ORF to a cell in vitro. The polynucleotide, expression cassette, and/or vector of the invention may be introduced to the cells in the appropriate amount. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the polynucleotide, expression cassette, and/or vector of the invention, e.g., virus vector, can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

The polynucleotide, expression cassette, and/or vector of the invention, e.g., virus vector, may be introduced to cells in vitro for the purpose of administering the modified cell to a subject. In particular embodiments, the cells have been removed from a subject, the polynucleotide, expression cassette, and/or vector of the invention, e.g., virus vector, is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the polynucleotide, expression cassette, and/or vector of the invention, e.g., virus vector, is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector ex vivo are administered to the subject in an effective amount in combination with a pharmaceutical carrier.

A further aspect of the invention is a method of administering the polynucleotide, expression cassette, and/or vector of the invention, e.g., virus vector, to a subject. In particular embodiments, the method comprises a method of delivering a CLN5 ORF to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^2$, $10^3$, $10^1$, $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more, e.g., about $10^7$, $10^8$, $10^9$, $10^{10}$, $10^{11}$, $10^{12}$, $10^{13}$, $10^{14}$, or $10^{15}$ transducing units, yet more preferably about $10^{10}$, $10^{11}$, $10^{12}$, $10^{13}$, $10^{14}$, or $10^{15}$ transducing units (TU). Doses and virus titer transducing units may be calculated as vector or viral genomes (vg).

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and on the nature of the particular vector that is being used. In some embodiments, more than one mode and/or route of administration may be utilized, for example, e.g., intraparenchymal administration and intracerebroventricular administration.

In some embodiments, the viral vector is administered to the CNS, the peripheral nervous system, or both.

In some embodiments, the viral vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intraparenchymal, intranasal, intra-aural, intra-ocular (e.g., intra-vitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the viral vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharm. Res. 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLES

Example 1: CLN5 Gene Therapy in CLN5$^{-/-}$ Borderdale Sheep

Sheep with naturally-occurring disease provide ideal models, being similarly sized to humans, weighing 3.5-4.5 kg at birth and growing to 80-110 kg adults. The gyrencephalic ovine brain is similar in physical organization to the human brain and in size to non-human primate brains, thus providing a good approximation for dose requirements, vector distribution and the utility of gene therapy strategies in pediatric neurodegenerative disorders. The executive function and cognitive capabilities of sheep are now being recognized and their longevity (9-12 years) allows monitoring of the clinical effectiveness and the longer term consequences of gene therapies over a time-frame relevant to disease. Since such trials take several years, and the downstream consequences of successful treatments will require monitoring, there is a pressing need to harvest translational data in vivo and allow successful trials to continue without prematurely sacrificing animals for post mortem neuropathological evaluation.

TABLE 4

Treatment Groups and Results

| Sheep | Genotype | Treatment and age given[a] | Total dose[b] | Gender[c] | Endpoint or current age, mo[d] | Clinical description | Seizures |
|---|---|---|---|---|---|---|---|
| 1100 | CLN5+/− | Untreated | — | F | 23.8 | Normal | − |
| 1103 | CLN5+/− | Untreated | — | M | 18.4 | Normal | − |
| 1105 | CLN5+/− | Untreated | — | F | 23.7 | Normal | − |
| 1106 | CLN5+/− | Untreated | — | F | 23.7 | Normal | − |
| 1118 | CLN5+/− | Untreated | — | M | 19 | Normal | − |

TABLE 4-continued

Treatment Groups and Results

| Sheep | Geno-type | Treatment and age given[a] | Total dose[b] | Gender[c] | Endpoint or current age, mo[d] | Clinical description | Seizures |
|---|---|---|---|---|---|---|---|
| 1121 | CLN5+/− | Untreated | — | M | 18.7 | Normal | − |
| 1128 | CLN5+/− | Untreated | — | M | 57.8 | Normal | − |
| 1107 | CLN5−/− | Untreated | — | M | 17.2 | Deceased, blind, advanced disease | + |
| 1109 | CLN5−/− | Untreated | — | F | 23.2 | Deceased, blind, advanced disease | + |
| 1110 | CLN5−/− | Untreated | — | F | 18.3 | Deceased, blind, advanced disease | + |
| 1114 | CLN5−/− | Untreated | — | M | 18.3 | Deceased, blind, neurological disease | − |
| 1115 | CLN5−/− | Untreated | — | M | 18.8 | Deceased, blind, advanced disease | + |
| 1116 | CLN5−/− | Untreated | — | M | 17.3 | Deceased, blind, advanced disease | + |
| 1122 | CLN5−/− | Untreated | — | F | 18.1 | Deceased, blind, advanced disease | + |
| 1102 | CLN5−/− | ICV scAAV9.CBh.CLN5; 3 mo | $1.7 \times 10^{12}$ | F | 30.6 | Alive, blind | − |
| 1111 | CLN5−/− | ICV scAAV9.CBh.CLN5; 3 mo | $1.7 \times 10^{12}$ | F | 30.5 | Alive, blind | − |
| 1128 | CLN5−/− | ICV scAAV9.CBh.CLN5; 3 mo | $1.7 \times 10^{12}$ | F | 30.5 | Alive, blind | − |
| 1104 | CLN5−/− | ICV scAAV9.CBh.CLN5; 3 mo | $5.0 \times 10^{12}$ | F | 27.4 | Deceased, advanced disease | − |
| 1120 | CLN5−/− | ICV scAAV9.CBh.CLN5; 3 mo | $5.0 \times 10^{12}$ | F | 30.5 | Alive, blind | − |
| 1123 | CLN5−/− | ICV scAAV9.CBh.CLN5; 3 mo | $5.0 \times 10^{12}$ | F | 30.5 | Alive, blind | − |
| 1164 | CLN5−/− | ICV scAAV9.CBh.CLN5; 7 mo | $4.0 \times 10^{12}$ | F | 41.6 | Alive, blind | − |
| 1165 | CLN5−/− | ICV scAAV9.CBh.CLN5; 7 mo | $4.0 \times 10^{12}$ | F | 22.3 | Deceased, blind, mild tremors | + |
| 1170 | CLN5−/− | ICV scAAV9.CBh.CLN5; 7 mo | $4.0 \times 10^{12}$ | F | 41.4 | Alive, blind | − |
| 1172 | CLN5−/− | ICV scAAV9.CBh.CLN5; 7 mo | $4.0 \times 10^{12}$ | F | 22.5 | Deceased, visual deficits | − |
| 1185 | CLN5−/− | ICV scAAV9.CBh.CLN5; 7 mo | $5.5 \times 10^{12}$ | F | 21.4 | Deceased, advanced disease | − |
| 1186 | CLN5−/− | ICV scAAV9.CBh.CLN5; 7 mo | $5.5 \times 10^{12}$ | F | 29.9 | Alive, blind | − |
| 1187 | CLN5−/− | ICV scAAV9.CBh.CLN5; 7 mo | $5.5 \times 10^{12}$ | F | 29.9 | Alive, blind, mild tremors | + |
| 1143 | CLN5−/− | ICV scAAV9.CBh.CLN5; 9 mo | $5.5 \times 10^{12}$ | F | 18.5 | Deceased, blind, advanced disease | + |
| 1163 | CLN5−/− | ICV scAAV9.CBh.CLN5; 9 mo | $5.5 \times 10^{12}$ | F | 30.2 | Alive, blind, mild tremors | + |
| 1165 | CLN5−/− | ICV scAAV9.CBh.CLN5; 9 mo | $5.5 \times 10^{12}$ | F | 21.7 | Deceased, blind, advanced disease | − |

[a] ICV, intracerebroventricular; scAAV9, self-complementary adeno-associated viral vector serotype 9; CBh, hybrid chicken β-actin promoter; mo, months
[b] Viral genomes (vg)
[c] M, male; F, female
[d] Untreated sheep were euthanised at their clinical humane endpoint. Treated sheep (boxed) remain alive unless indicated The following materials and methods were used in published trials of CLN5 gene therapy in Borderdale sheep (Mitchell et al., 2018 *Mol. Ther* 26: 2366-2378).

Animals. Borderdale sheep were diagnosed at birth and maintained at Lincoln University under US National Institutes of Health guidelines for the care and use of animals in research and the NZ Animal Welfare Act (1999). All experimental protocols were approved by the Lincoln University Animal Ethics and Institutional Biosafety Committees. Table 4 summarizes the study design. Six $CLN5^{-/-}$ pre-clinically affected lambs received bilateral intracerebroventricular (ICV) injections of self-complementary (se) AAV9 vectors (scAAV9, n=6) encoding ovine CLN5 at 3 months. In two separate trials, four and then three lambs with mild clinical signs of disease received bilateral ICV injections of scAAV9-CLN5 at 7 months. Finally, another three $CLN5^{-/-}$ sheep with more advanced disease symptoms were treated with ICV scAAV9-CLN5 at 9 months. Treated sheep were maintained under normal outdoor pastural conditions, as were all age-matched $CLN5^{+/-}$ unaffected and untreated affected $CLN5^{-/-}$ control sheep.

Vectors. Recombinant self-complementary AAV9, expressing codon-optimized ovine CLN5 under the control of the CBh promoter (scAAV-CLN5) (wildtype ovine CLN5 GenBank accession number NM_001082595), was produced by the University of North Carolina *Gene Therapy Center Vector Core* (NC, USA) by triple transfection of HEK293 cells, iodixanol gradient centrifugation and ion-exchange chromatography. Vectors were formulated in 350 mM PBS containing 5% sorbitol, and titers determined by quantitative PCR[38].

Vector delivery. Stereotactic surgical procedures were used as described (Linterman et al., 2011 *Hum. Gene Ther.* 22: 1011-1020). All sheep received bilateral injections of 400 µl scAAV9-CLN5 into the lateral cerebral ventricles, via two burr holes. Lambs treated at 3 months received a total dose of either $1.7 \times 10^{12}$ (n=3) or $5.0 \times 10^{12}$ (n=3) viral genomes (vg). Clinically affected $CLN5^{-/-}$ sheep each received $4.0 \times 10^{12}$ vg at 7 months (n=4) or $5.5 \times 10^{12}$ vg at 6 and 9 months (n=3 each).

Neurological Examination. Physical and neurological clinical assessments were performed monthly on the treated sheep and cohorts of healthy $CLN5^{+/-}$ controls and untreated $CLN5^{-/-}$ sheep. An ovine-specific Batten disease rating scale (oBDRS) (Table 5) was developed, similar to those used for human NCLs (Marshall et al., 2005 *Neurology* 65: 275-279; Simonati et al., 2017 *Dev. Med. Child Neurol.* 59: 815-821). Body condition scores and weights were recorded. Mentation, gait, head carriage and postural traits, as well as manifest tremors or seizure onsets, were reported in conjunction with cranial nerve function tests. Each parameter was scored from 4 to 0 (normal to abnormal) by two blinded investigators, based on the degree of deviation from healthy function, scores averaged when there was a discrepancy, and then combined to give a total out of 40.

Electroretinography. Electroretinography (ERG) was performed on the treated sheep every 2-3 months until retinal function was lost. Mixed receptor response ERG recordings were obtained from each eye after 5 min. of dark adaptation using an Eickemeyer Veterinary ERG system (Eickemeyer—Medizintechnik für Tiersrzte KG, Tuttlingen, Germany) and compared with untreated $CLN5^{+/-}$ and $CLN5^{-/-}$ controls.

Maze Testing. Sheep cognition was assessed monthly via performance in a closed-field maze (FIG. 2A) under daytime photopic light and the times required to traverse the maze recorded. Sheep negotiated the maze five times on each testing day and were fitted with harness-attached GPS loggers to collect their position in the maze arena every second. Monthly testing continued until the sheep were unable to complete the maze.

Quantitative analysis of brain atrophy. Brain CT imaging of sheep anaesthetized by intravenous injection of 0.8 mg/kg live weight diazepam (Pamlin injection, Troy Laboratories NZ Pty Ltd, Auckland, NZ) and 17 mg/kg live weight of ketamine hydrochloride (Phoenix Ketamine injection, Phoenix Pharm Distributors Ltd, Auckland, NZ) was carried out bimonthly. Coronal slices were acquired at 1 mm intervals, 120 kV, 100 mA, 2 s rotation time on a GE Prospeed CT scanner (GE Healthcare, Hyugo, Japan). Three-dimensional (3D) modelling and intracranial volumetrics were performed using the 3D slicer 4.3.1 freeware (slicer.org). That intracranial volumes are good surrogates for brain volumes was confirmed by comparing the scanned volumes of healthy control (n=14) and NCL affected (n=11) at post mortem with the volumes of the removed brains measured by water displacement[16].

Immunohistochemistry. Methods were similar to those previously described. Brains were perfusion-fixed via the carotid artery with 10% formalin in 0.9% NaCl at post mortem. After equilibration in 20% sucrose and 10% ethylene glycol in 0.9% NaCl for 7 days, brain hemispheres were frozen at −80° C. Sequential 50 µm sagittal sections were cut on a sliding microtome (Microm International, Walldorf, Germany) and stored at −20° C. in 96-well plates in cryoprotectant (phosphate buffered saline (PBS) containing 30% ethylene glycol, 15% sucrose and 0.05% sodium azide). Antibodies were diluted in 10% normal goat serum (NGS) in PBS, pH 7.4, containing 0.3% Triton X-100 (Sigma Aldrich) (PBST). Test sections were thawed, blocked with 1% $H_2O_2$ in PBST, 30 min, then 1 h in 15% NGS, prior to overnight incubation in rabbit polyclonal anti-CLN5 (Dr. Stephanie Hughes, University of Otago; 1:500). Immunoreactivity was detected using biotinylated goat anti-rabbit IgG (Sigma-Aldrich, B7389; 1:1,000), 4 hr, followed by ExtrAvidin peroxidase (Sigma-Aldrich, E2886, 1:1000), 4 h. Staining was visualized using 0.5 mg/ml 3,3'-diaminobenzidine (DAB; Sigma-Aldrich, D5637) and 0.01% $H_2O_2$ in PBS.

Statistics. One-way ANOVA was used to assess the statistical significance of differences between the control and treatment groups (GraphPad Prism 7 Software, La Jolla, California, USA). Pairwise comparisons were then performed between treatment groups using the Mann-Whitney test or Student's t-test as indicated. Data are expressed as means±SEM. P≤0.05 was considered significant.

Example 2: scAAV9 Delivery of CLN5 Construct in Pre-Clinically Affected Borderdale Sheep Tolerance to CLN5 Gene Transfer by the Pre-clinically Affected Sheep. Six $CLN5^{-/-}$ affected sheep received intracerebroventricular injections of scAAV9 vector expressing ovine CLN5 at 3 months of age, before the onset of clinical disease (Table 4). Their rectal temperatures, pulse and respiratory rates remained normal throughout the three-week post-injection observation period and no behavioural changes or clinical signs of an immune response were observed in these sheep monitored daily for two years after these single neurosurgical procedures. Five of the six treated sheep currently remain alive in the field free of disease signs at 30 months of age, except for a much delayed onset of visual deficits, and have well exceeded the ~22 month maximal life expectancy of untreated $CLN5^{-/-}$ sheep. One treated sheep (1104) developed stereotypical disease, albeit delayed, and was euthanized at 27.4 months. Neuropathological assessment is underway for this animal. The materials and methods used in this trial are described in Example 1 (Mitchell et al., 2018 *Mol. Ther* 26: 2366-2378).

Clinical Efficacy of CLN5 Gene Transfer to Pre-clinically Affected Sheep. The long-term clinical benefit was assessed monthly against CLN5 heterozygous ($CLN5^{+/-}$) and untreated $CLN5^{-/-}$ sheep using an ovine-specific Batten disease rating scale (oBDRS; Table 5), similar to those used for human NCLs. The oBDRS was developed to monitor the natural progression of the disease longitudinally and to allow assessment of the clinical efficacy of therapies trialled in sheep. Ten parameters were scored monthly from 4 to 0 (normal to abnormal) to give a combined score out of 40. Lower scores reflect greater impairment.

TABLE 5

Ovine-specific Batten disease rating scale (oBDRS)

(i) Physical assessments
A. Abnormalities in sensation
1. Visual function/acuity

| | |
|---|---|
| 4 | Normal |
| 3 | Early signs-head tilt, stargazing, wariness of shadows |
| 2 | Mild difficulty-decreased/lost menace response, loss of visual tracking/ocular pursuit |
| 1 | Moderate difficulty-decreased PLR and/or ERG, possible funduscopic changes |
| 0 | Severe disturbance-minimal PLR, absent dazzle response, flatline ERG, obvious funduscopic changes, runs into objects |

Method: Observation in the field, maze or when held; menace and dazzle responses, corneal, palpebral and pupillary light reflexes (PLR); funduscopy; electroretinography (ERG) assessment 2. Auditory function

| | |
|---|---|
| 4 | Normal, vigilant |
| 3 | Early signs-unaware of approach at 10 m |
| 2 | Mild difficulty-unaware of approach at 5 m |
| 1 | Moderate difficulty-decreased startle response, unaware of approach at 1-2 m |
| 0 | Severe disturbance-lost startle response |

Method: Observation in the field or maze; spontaneous startle with auditory stimuli (e.g. calling out, whistling, clapping)

B. Abnormalities in body, posture or movement
3. Overall body movement, gait and posture

| | |
|---|---|
| 4 | Normal |
| 3 | Early signs-low head carriage, propensity to stumble, crouch, or baulk in race |
| 2 | Mild difficulty-feet dragging, impaired ascent/descent of stairs and ramps |
| 1 | Moderate difficulty-ataxia, hypermetria, wide stance, proprioceptive and motor deficits |
| 0 | Severe disturbance-hindlimb paresis, akinesia, immobile |

Method: Observation in the field, maze, yard and on stairs

4. Localized muscle tremors (e.g. ear, eyelid, lip, hindlimb) at rest

| | |
|---|---|
| 4 | Absent |
| 3 | Early signs-slight and infrequent motor tics |
| 2 | Mild in amplitude and persistent, or moderate in amplitude but intermittently present |
| 1 | Moderate in amplitude and present most of the time |
| 0 | Severe tetanic seizures-marked in amplitude, present most of the time and interferes with most activities |

Method: Observation in the field whilst not under stress

5. Inducible or action muscle tremors

| | |
|---|---|
| 4 | Absent |
| 3 | Early signs-slight and infrequent motor/myoclonic tics |
| 2 | Mild in amplitude and persistent, or moderate in amplitude but intermittently present |
| 1 | Moderate in amplitude and present most of the time |
| 0 | Severe tetanic seizures-marked in amplitude, present most of the time and interferes with most activities |

Method: Observation in the maze or yard whilst handling/moving and under stress

6. Body condition scoring

| | |
|---|---|
| 4 | Normal |
| 3 | Slight but noticeable loss in body weight (−1 kg) |
| 2 | Mild loss in condition (−0.5) or body weight (−2 kg) |
| 1 | Moderate loss in condition (−1) or body weight (−3 kg) |
| 0 | Severe loss in condition (>1 loss) or body weight (>3 kg) |

Method: Body condition scoring and live weight measurement (ii) Behavioural assessments
7. Mentation

| | |
|---|---|
| 4 | Normal |
| 3 | Early signs-isolated incidences of somnolence, some confusion |
| 2 | Mild difficulty-periods of somnolence and self-segregation, reduced herding |
| 1 | Moderate difficulty-sustained somnolence and low mentation, dull when handled |
| 0 | Severe disturbance-depression, lethargy or somnolence with vegetative symptoms (e.g. anorexia, weight loss), non-responsiveness to external stimuli |

Method: Observation in the field, maze or when handled

TABLE 5-continued

Ovine-specific Batten disease rating scale (oBDRS)

8. Behaviour

4 Normal
3 Early signs-undefined and/or isolated episodes of abnormal behaviour
2 Mild stereotyped or repetitive activities
1 Moderate stereotyped or repetitive activities
0 Severe stereotyped or repetitive activities, including feeding abnormalities
Method: Observation in the field, maze or yard. Record any abnormal behaviour (e.g. heightened vocalization), stereotyped/repetitive behavior (e.g. aimless or compulsive circling or wandering, teeth grinding) or feeding abnormalities (e.g. dribbling, sham grazing/drinking)

9. Aggression

4 Normal
3 Slight aggression to self and/or others
2 Mild aggression to self and/or others
1 Moderate aggression to self and/or others
0 Severe aggression to self and/or others
Method: Observation in the field, maze or yard. Aggressive behaviors include stomping, fence jumping, wool biting and head butting into other sheep, fences or pens 10. Capability/independence 4 Normal, completely independent
3 Early signs-slow to move but otherwise independent
2 Mild loss-obvious clinical phenotype but independent
1 Moderate loss but still sustainable on open pasture
0 Severe loss-totally dependent and requires extensive indoor nursing As expected for a recessive disease, $CLN5^{+/-}$ carriers were clinically normal throughout the study, consistently scoring 40 (FIG. 1A). Sheep treated before the development of any disease signs also showed no functional deficits, being clinically indistinguishable from healthy $CLN5^{+/-}$ controls for the first 18 months while oBDRS scores for the untreated CLN5-~ sheep decreased to under 15, reflecting the natural progressive disease course.

Figure 1B:
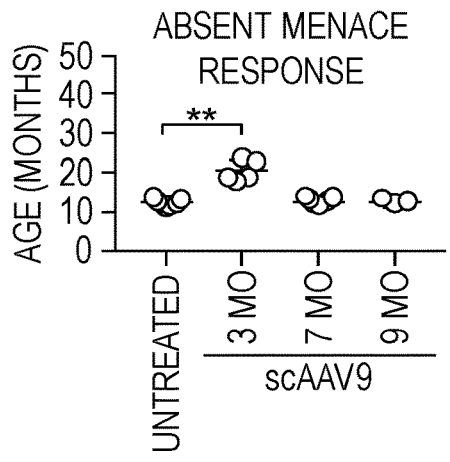

This successful trial was extended to determine any longer term consequences following treatment. A much-delayed loss of vision, apparent by 19-25 months, was the only disease manifestation noted. Funduscopic examination revealed intermediary indicators of retinal damage, mild tapetal hyperreflectivity and blood vessel attenuation at this time. Concomitant menace response deficits account for the deviation from normal observed on the oBDRS from 20 months (FIGS. 1A-1B). Much delayed functional blindness (absent menace response) ensued (untreated $CLN5^{-/-}$ sheep: 12.6±0.4 months, scAAV9-treated sheep: 20.5±1.3 months, P<0.001) (FIG. 1B). At 25 months pupillary light reflexes were sluggish in the treated sheep and electroretinogram (ERG) responses from the scAAV9-treated sheep were severely diminished, similar to those seen in untreated $CLN5^{-/-}$ sheep at 15-17 months (FIG. 8A).

The treated sheep are otherwise phenotypically normal at 31 months. They are alert and highly interactive with their environment, and have developed strong social attachments within their cohort and with animal care personnel, interacting through vocalization and physical contact and detecting the presence of foreign sheep or humans immediately. When grazing in the open field they show no evidence of the stereotypical behaviour, reduced mentation, wide stance, manifest ataxia and hind limb paresis or localized seizure activity seen in the advanced stages of ovine CLN5 disease (FIGS. 1D-1G).

In stark contrast, stereotypical disease progression had already commenced in the untreated $CLN5^{-/-}$ cohort at 6 months (FIGS. 1A-1G). Initial manifestations were apprehensive walking with a low head carriage and baulking when in shadows, passing through gateways or negotiating steps. Vision deteriorated and by 13 months untreated animals were functionally blind, exhibiting a bilateral absence in menace response, loss of visual tracking and a decreased acoustic startle which affected their ability to flock. Proprioceptive and motor deficits progressed to a wide stance, hind-limb ataxia, stumbling, and intermittent episodes of localized muscle tremors, particularly of the ears, eyelids, lips and limbs. Behavioural changes included self-segregation, repetitive actions such as aimless circling, and feeding abnormalities including dribbling and sham grazing. From 15 months they lost body condition and demonstrated low mentation, extended periods of somnolence and poor or no responses to a variety of stimuli including loud noises, flashing lights and approaching humans. Extremely hyper-reflective foci in the retina were obvious to the naked eye and funduscopy showed thinned retinal vasculature, together indicative of photoreceptor damage. The neurological phenotype from 17 months was accompanied by tremors ranging from subtle to whole-body inducible seizures, defining their humane endpoint.

Figure 5:
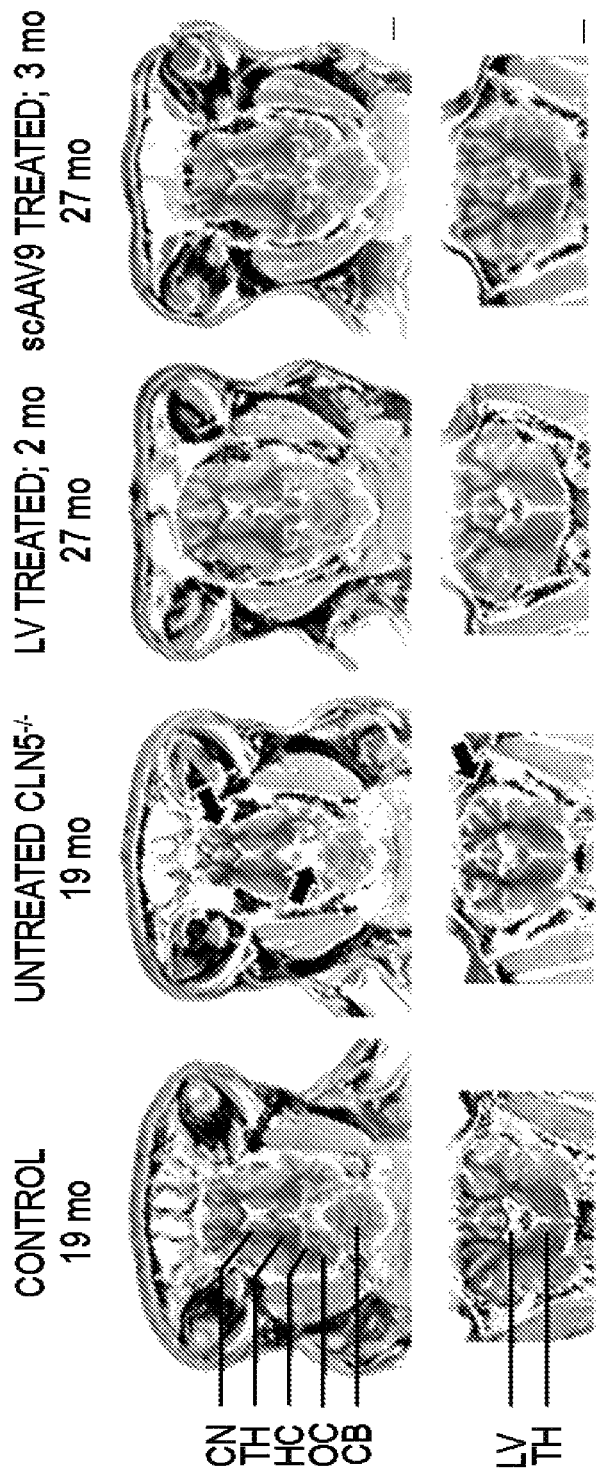
FIG. 5 shows MRI imaging confirming preservation of neuroanatomical structure after pre-clinical CLN5 gene therapy with lentiviral (LV) or ssAAV9 vectors. Volumetric T1-weighted MR images in the horizontal (top) and coronal (bottom) views of a 19-month-old healthy CLN5$^{+/-}$ control and an untreated CLN5$^{-/-}$ sheep brain, compared with brains from much older (27 months) sheep that have received LV or ssAAV9-CLN5 gene therapy before the development of clinical signs. Similar results have been observed after pre-clinical scAAV9-CLN5 gene therapy (data not shown). Treatment with all three vector platforms preserved neuroanatomical structure, protecting against the profound cortical atrophy (upper arrow), prominent ventricular enlargement (middle arrow) and cranial thickening (lower arrow) seen in the untreated CLN5' brain. Scale bar represents 1 cm. CB, cerebellum; CN, caudate nucleus; HC, hippocampus; LV, lateral ventricle; OC, occipital cortex; Th, thalamus.

Similar results have been seen with the pre-clinical delivery of ovine CLN5 in sheep using two other viral vector platforms—lentivirus and single-stranded (ss) AAV9. Treatment at 3 months of age with LV-CLN5 or ssAAV9-CLN5 prevented stereotypical disease onset and development (Mitchell et al., 2018 *Mol. Ther* 26: 2366-2378). Maze testing and the oBDRS were employed to show preservation of neurological and cognitive function, whilst computed tomography and magnetic resonance imaging (MRI) revealed normal brain structures and stabilized intracranial volumes (FIG. 5; Mitchell et al., 2018 *Mol. Ther* 26: 2366-2378). The treated sheep went blind but the onset of visual deficits was again much delayed. One ssAAV9-treated animal remained alive in the field until 62 months of age, almost triple the lifespan of untreated CLN5-affected sheep.

Figure 2A:
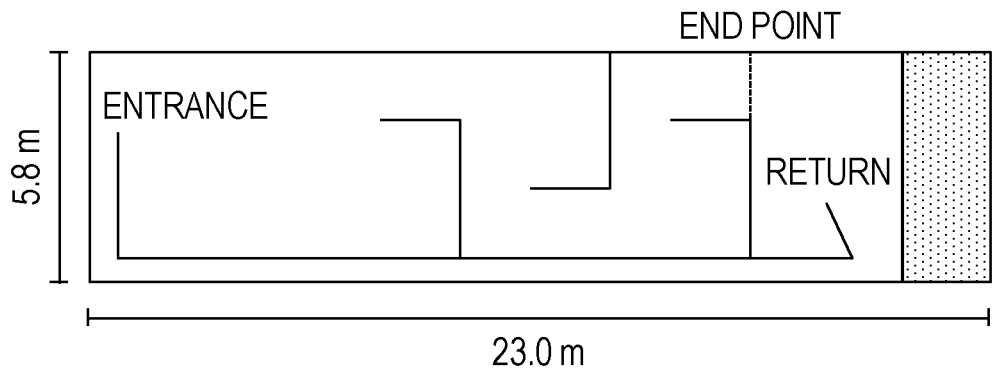
FIGS. 2A-2B shows CLN5 gene therapy delays the onset of cognitive deficits in CLN5 affected sheep. Vision and cognition were assessed in closed field mazes.
Figure 2B:
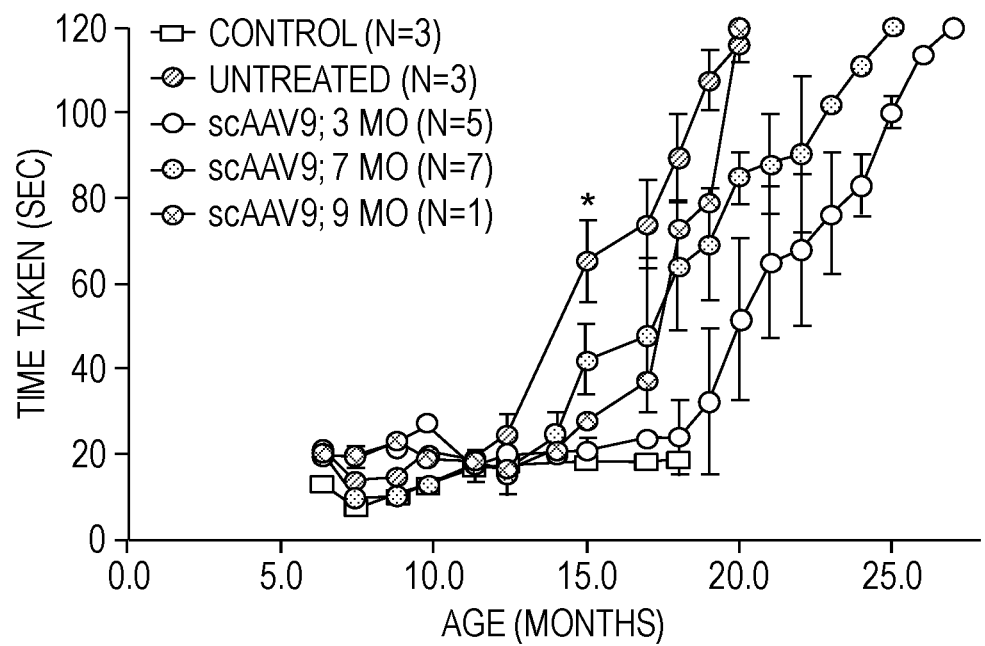

Functional Efficacy of CLN5 Gene Transfer to Pre-clinically Affected Sheep. Cognitive decline was assessed in a closed-field maze test which relied on the natural flocking instinct of sheep to motivate passage to conspecifics penned in a goal area (FIGS. 2A and 2B). No difference in maze performance was discernible between 3-month treated sheep and healthy CLN5+1 sheep until 19 months of age (FIG. 2B). Treated sheep walked or ran through the maze with their heads held high, avoiding the obstacles and error zones, at traverse times usually faster than the heterozygote controls. The effects of their treatment-delayed visual loss surfaced from 19-26 months and traverse times and failure rates increased (FIGS. 2A and IC) and they began to collide with maze obstacles. This prompted the humane completion of the maze test.

Untreated CLN5$^{-/-}$ sheep showed a progressive navigational decline (FIG. 2A) and an affected phenotype from an early age. Despite their deteriorating vision (FIG. 1B), they were able to negotiate the maze for another few months (FIG. 1C), albeit at progressively longer traverse times. By 16 months they failed to transit the error zone or became too akinesic to complete the maze and testing was abandoned. They still tended to avoid obstacles, pulling up short, but failed to find a way around.

Figure 3:
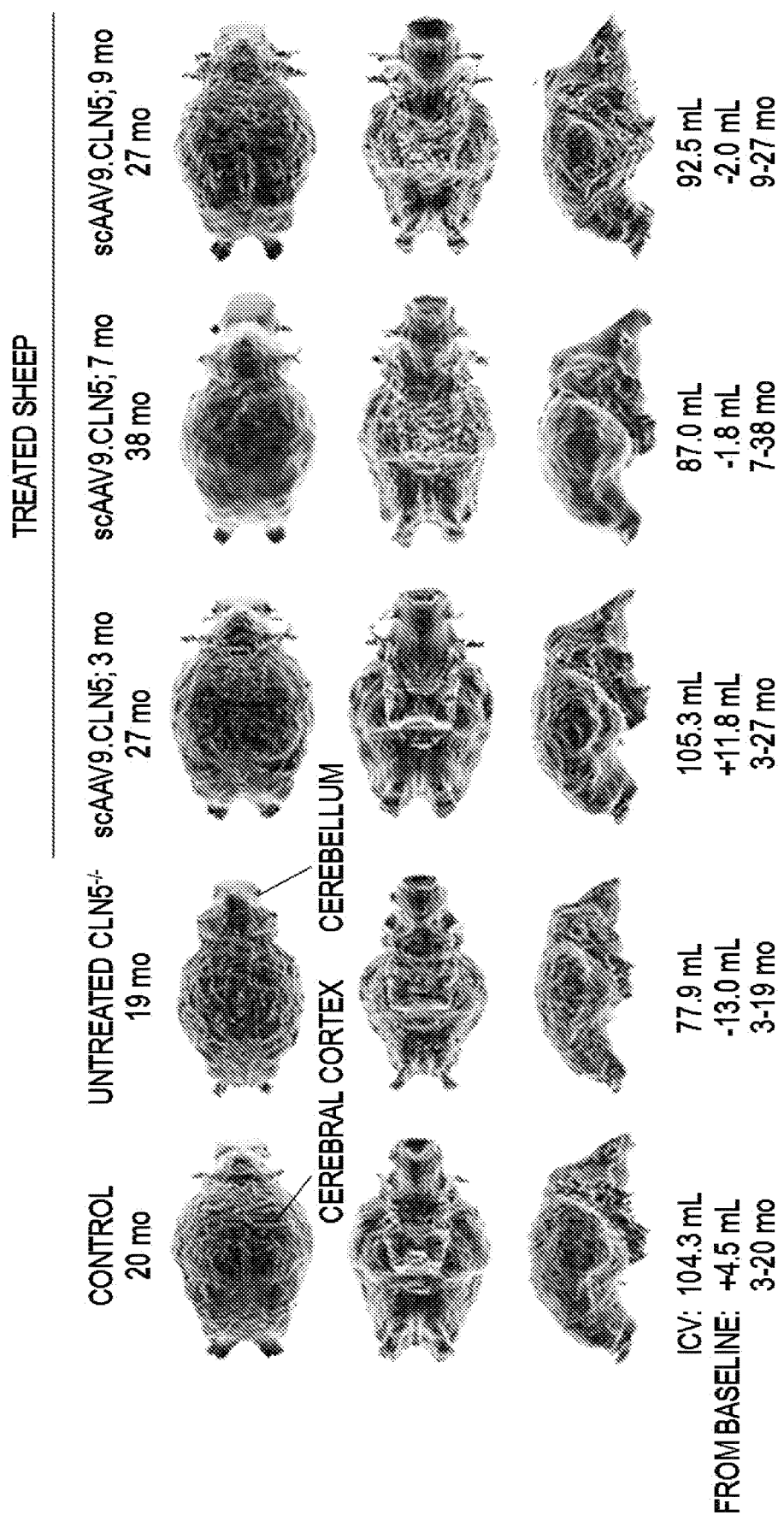
FIG. 3 shows three-dimensional modelling of gross neuroanatomy after CLN5 gene therapy. Representative three-dimensional models of the sheep cranium reconstructed from CT images showing no discernible differences in the gross anatomy of the treated brains at 27-38 months compared with a healthy CLN5$^{+/-}$ control. All lacked the pronounced atrophy visible in the younger untreated CLN5-1 cerebral cortex at 19 months. Note the relative sparing of the affected cerebellum. Intracranial volume (ICV) was normalized after scAAV9-CLN5 delivery at 3 months, whilst CLN5 gene therapy at 7 months or 9 months minimized ICV loss from baseline (time of injection). Scale bar represents 2 cm.

Maintenance of Brain Volume and Structure after CLN5 Gene Transfer to Pre-clinically Affected Sheep. Three-dimensional reconstructions from longitudinal computed tomography (CT) scanning were used to monitor brain atrophy in vivo and revealed the corrective effect of preclinical CLN5 gene therapy (FIG. 3). Treated brains maintained the structural appearance of healthy control brains with no evidence of the atrophy characteristic of untreated CLN5$^{-/-}$ brains, particularly the notable degeneration of the occipital and parietal cortices which generalizes to the entire cortical mantle by 19 months.

Figure 4:
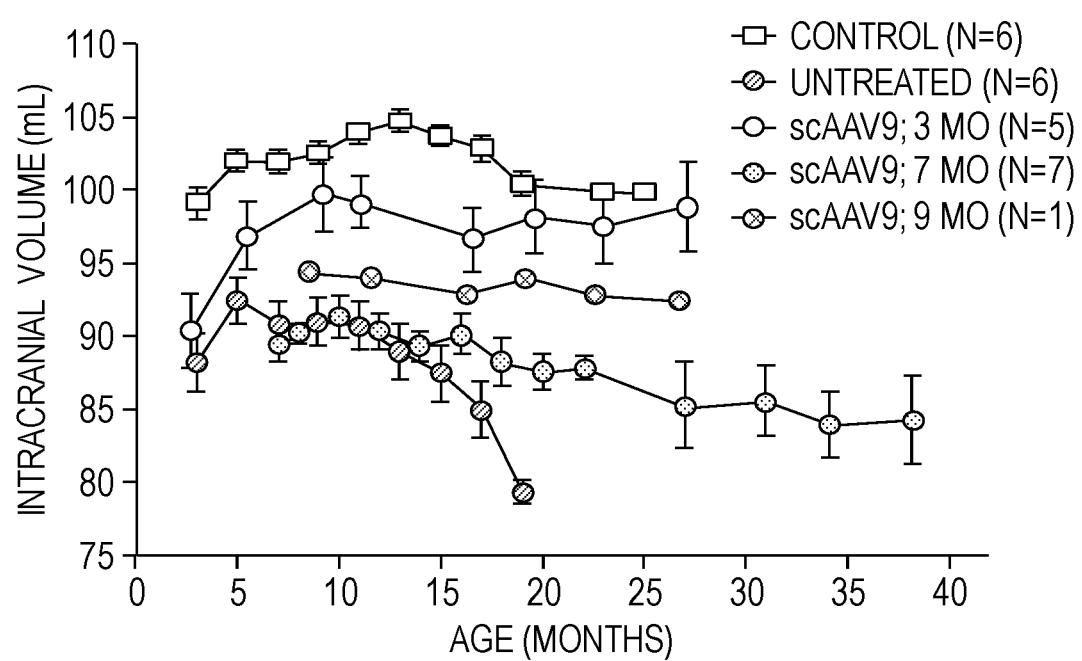
FIG. 4 shows normalization or stabilization of intracranial volumes by in vivo neuroimaging after CLN5 gene therapy. Longitudinal CT scans of treated sheep brains were compared against control data. Intracranial volume (ICV) was normalized after pre-clinical CLN5 gene therapy at 3 months. Extended volumetric retention was observed in all sheep treated at an early clinical stage (7 months) and one animal treated at an advanced disease stage (9 months) compared with the on-going atrophy of the untreated affected brains. One of the 3 mo. and two of the 9 mo. treated sheep showed brain atrophy, albeit delayed, and ultimately succumbed to the disease (data not shown). All data are expressed as means±SEM.

Treatment with scAAV9 attenuated volume loss, with treated brains growing to normal levels (FIGS. 3 and 4). This contrasted with the atrophic shrinkage of the untreated CLN5$^{-/-}$ brains.

The lentiviral, and ssAAV9 trials are the first to demonstrate the efficacy of viral-mediated CLN5 gene therapy in a large animal model of NCL, using outcome measures adapted from human medicine (Mitchell et al., 2018 *Mol. Ther* 26: 2366-2378). We then followed this study up, testing scAAV9-CLN5 delivery to pre-clinical 3-month-old CLN5$^{-/-}$ sheep. All lentiviral (n=3), ssAAV9 (n=3), and five out of six scAAV9-treated sheep were blind but otherwise clinically indistinguishable from unaffected controls on the oBDRS at 27 months of age. Their quality of life was profoundly improved and they well exceeded the typical lifespan of untreated animals (maximum 22 months). Longitudinal neuroimaging and 3-D modelling has shown that the treated brain structure, architecture and size was normalized, regardless of vector platform. Five of the LV and ssAAV9 treated sheep were euthanized at 27 months to allow a comparative post mortem assessment of CLN5 expression between the two vectors, and to look for pathological correction or any chronic immune response over time. A manuscript with these results is in preparation, showing attenuation of disease-related neuropathology from the time of injection. Five of the six sheep similarly treated pre-clinically at 3 months of age with scAAV9-CLN5 are still alive in the field at 31 months of age. They are blind but otherwise phenotypically normal. In vivo monitoring of them continues, looking for any further peripheral disease signs given the current level of central nervous system correction.

Example 3: scAAV Delivery of CLN5 Construct in Clinically Affected Borderdale Sheep Disease Progression Halted after CLN5 Gene transfer to Clinically Affected Sheep. Two further studies tested the efficacy of CLN5 gene therapy in sheep with established disease (Table 4). Firstly, seven 7-month-old CLN5$^{-/-}$ sheep, with evident brain atrophy and early clinical signs, received intracerebroventricular injections of scAAV9-CLN5 (Mitchell et al., 2018 *Mol. Ther* 26: 2366-2378). Next, three 9-month-old CLN5$^{-/-}$ sheep, with established brain atrophy and clinical disease, received intracerebroventricular injections of scAAV9.CLN5. The treatment was well tolerated and aside from visual loss there was a paucity of evidence of further disease progression in most treated sheep. Three of the seven 7-month-old treated sheep were euthanized at 23 months for neuropathological analyses, one of these having advanced disease symptoms, but the other four remain alive and well at 30-41 months. The materials and methods used in this trial are described in Example 1 (Mitchell et al., 2018 *Mol. Ther* 26: 2366-2378).

Clinical efficacy was monitored monthly on the oBDRS (FIG. 1A). The 7-month old sheep already had a mild clinical phenotype at enrolment, including a slight head tilt and/or low head carriage, wariness of shadows and they crouched when travelling through a confined gateway and these deficits were even more pronounced in the 9-month-old treated cohort. Unlike the sheep treated at 3 months of age, vision loss was not delayed for the 7 and 9 month treated animals. These sheep lacked menace responses by 12-14 months as do untreated CLN5$^{-/-}$ sheep (FIG. 1B). ERG amplitudes were extinguished in one 7-month treated sheep by 14 months, another five retained a response until 20 months, while the seventh had positive photopic and scotopic responses to 22 months (FIG. 8B). Two of the 9-month treated sheep retained ERG recordings until 19 months, and the third had a flatline ERG recording at 24 months.

Strikingly, there has been no dramatic advance in motor, neurological or behavioural dysfunction in the 7-month scAAV9 treated cohort from 12 to 41 months. Two sheep (1165, 1185) had short periods of heightened somnolence and exhibited inducible facial ties and mild circling behaviour on stress prior to euthanasia at 23 months but the collective oBDRS scores of the remaining treated sheep have not dropped below 25 (FIG. 1A). To compare, age-matched untreated CLN5$^{-/-}$ flock-mates developed stereotypical CLN5 disease with manifest seizures and negative ERGs from 16-22 months prompting euthanasia at 18-23 months when oBDRS scores ranged from 12.5-11.5 (FIG. 1A). One of the 9-month treated animals (1163) also remains alive in the field at 31 months of age, with mild tremors and loss of vision but little further clinical progression since injection. The other two 9-month treated animals did not respond as well, developing advanced disease which prompted their humane euthanasia at 19-22 months of age.

Figure 1C:
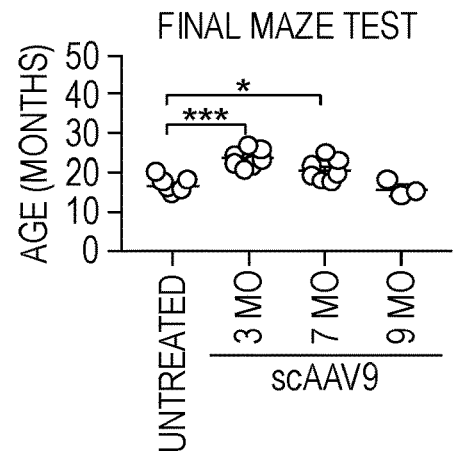
Figure 1D:
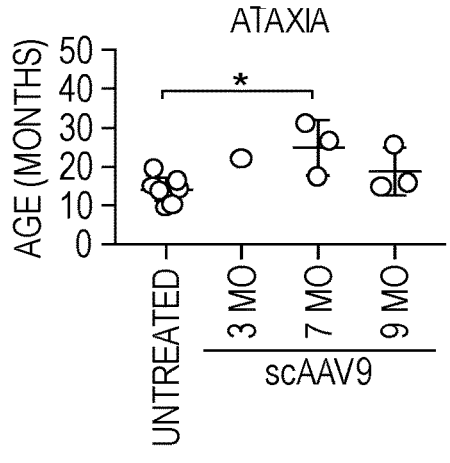
Figure 1E:
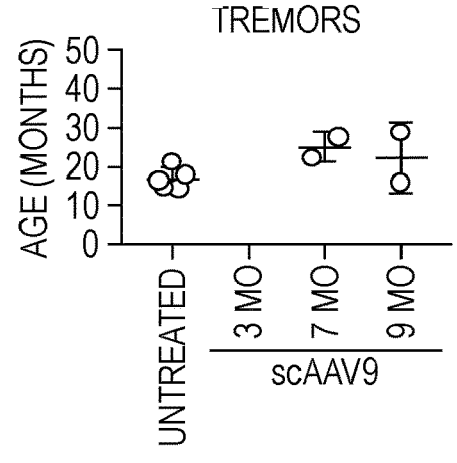
Figure 1F:
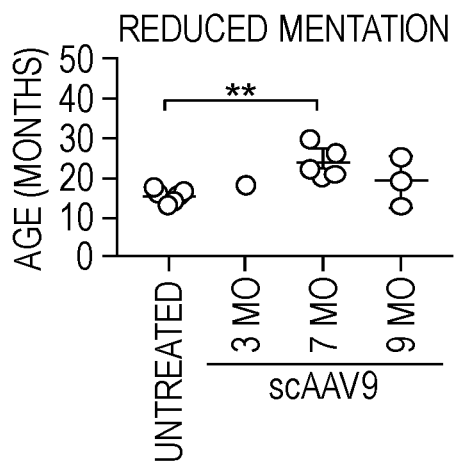
Figure 1G:
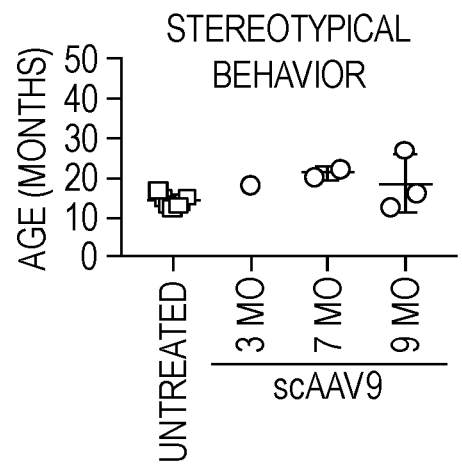

Sheep on this second trial received monthly maze testing (FIG. 2B). Maze traverse times of the untreated CLN5$^{-/-}$ sheep reflected their progressive slowing and ultimate failure while all of the 7-month and one of the 9-month scAAV9 treated sheep (1163) retained speed and the ability to traverse for longer, albeit to varying extents (FIGS. 2B and 1C). The 7-month treated sheep with ERG amplitudes extinguished at 14 months (1165 and 1185) struggled to complete the maze thereafter yet the other seven still completed most or all of the five maze runs within the allocated 120 sec at 19 months. Two of these sheep (1164 and 1170) were removed from the monthly testing regime at 24-25 months when they could no longer traverse the maze.

Figure 6:
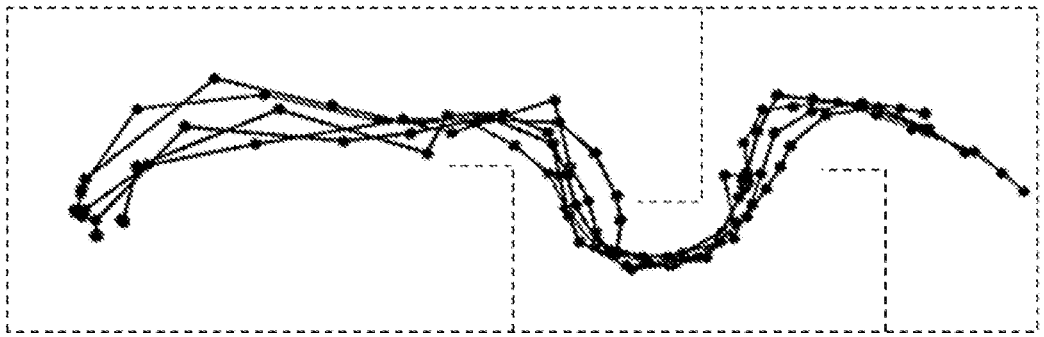
FIG. 6 shows GPS tracking of traversal through a closed field maze and highlighted the delay in cognitive decline after CLN5 gene therapy to clinically affected sheep. GPS positional data were collected at 1 second intervals (dots) and five traverses through the close field maze (FIG. 2B) plotted for a representative healthy CLN5$^{+/-}$ control, an untreated CLN5$^{-/-}$ sheep and a sheep treated with scAAV9-CLN5 at 7 months. The direct trajectory of the CLN5$^{+/-}$ sheep persisted throughout the testing, while untreated CLN5$^{-/-}$ sheep showed a less uniform path as early as 8 months with compulsive circling and ultimate failure by 19 months.
Figure 6:
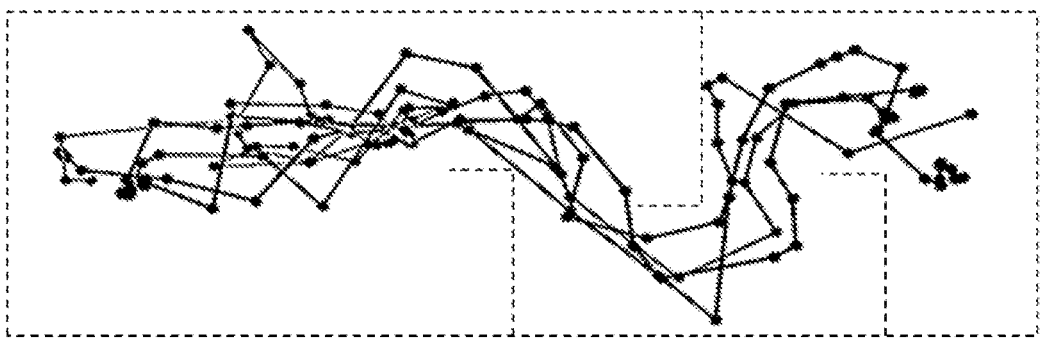
Figure 6:
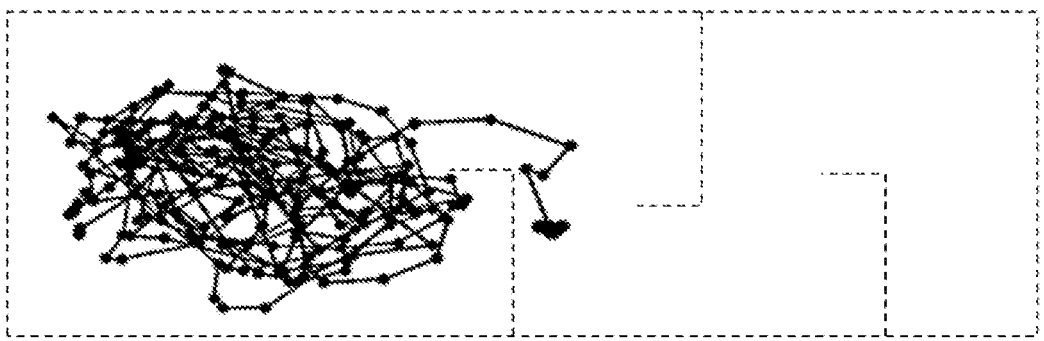
Figure 6:
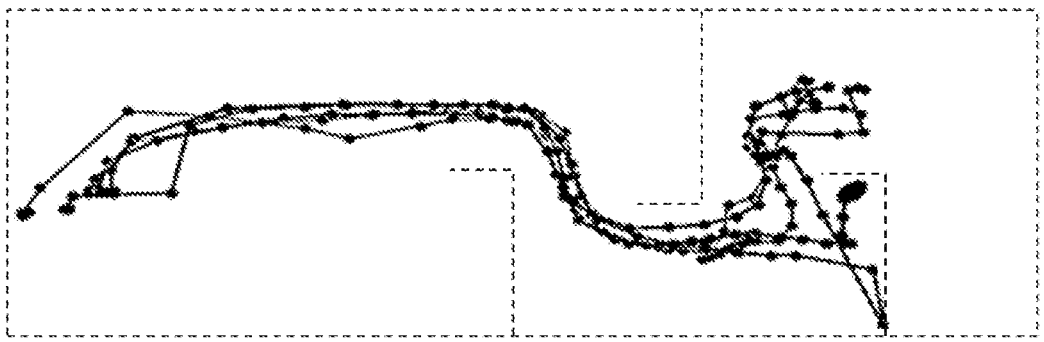

Sheep in this maze wore harness-attached global positioning system (GPS) units to track their movements (FIG. 6). Healthy CLN5$^{+/-}$ control sheep followed a uniform track through the maze with few pauses, avoided obstacles, and reached conspecifics in the goal area quickly. Initially, treated sheep also followed the most direct route. With time they found it harder to enter or exit the maze but still completed most of their runs until 24 months. In contrast, untreated CLN5$^{-/-}$ sheep took longer and a more random path from as early as 8 months. As their disease progressed, they lost any social and/or exploratory behaviour and would just stand in the maze arena bleating. By 19 months they circled compulsively in the start area (FIG. 6) or were too affected to participate in the testing (FIG. 1C).

Longitudinal CT scanning has indicated little post-injection brain atrophy in the scAAV9 treated sheep to date. Average intracranial volumes for the 7-month treated cohort fell from 89.5±1.2 mL pre-injection to plateau at 87.8±0.8 mL at 22 months (all seven animals), before falling to 85.3±3.0 mL at 27 months (five animals) and remains at 84.3±0.3 mL at 38 months for the two remaining animals of this age (FIG. 4). One animal has only lost 1.8 mL from baseline (7 months) to last scan (38 months) (FIG. 3). Treated brains actually increased in size over the first three months post-injection before mild volume loss began but this contrasts the rapid atrophy seen in untreated CLN5$^{-/-}$ sheep which causes a loss of 13±1.3 mL of intracranial volume from 3 to 19 months.

scAAV9-CLN5 delivery at 9 months did not stop stereotypical brain atrophy in two of three CLN5 affected animals but intracranial volumes for the third (1163) have been maintained at near pre-injection values. Between 9 months (injection) and 27 months this animal has only lost 2 mL of intracranial volume (FIGS. 3 and 4).

Figure 7:
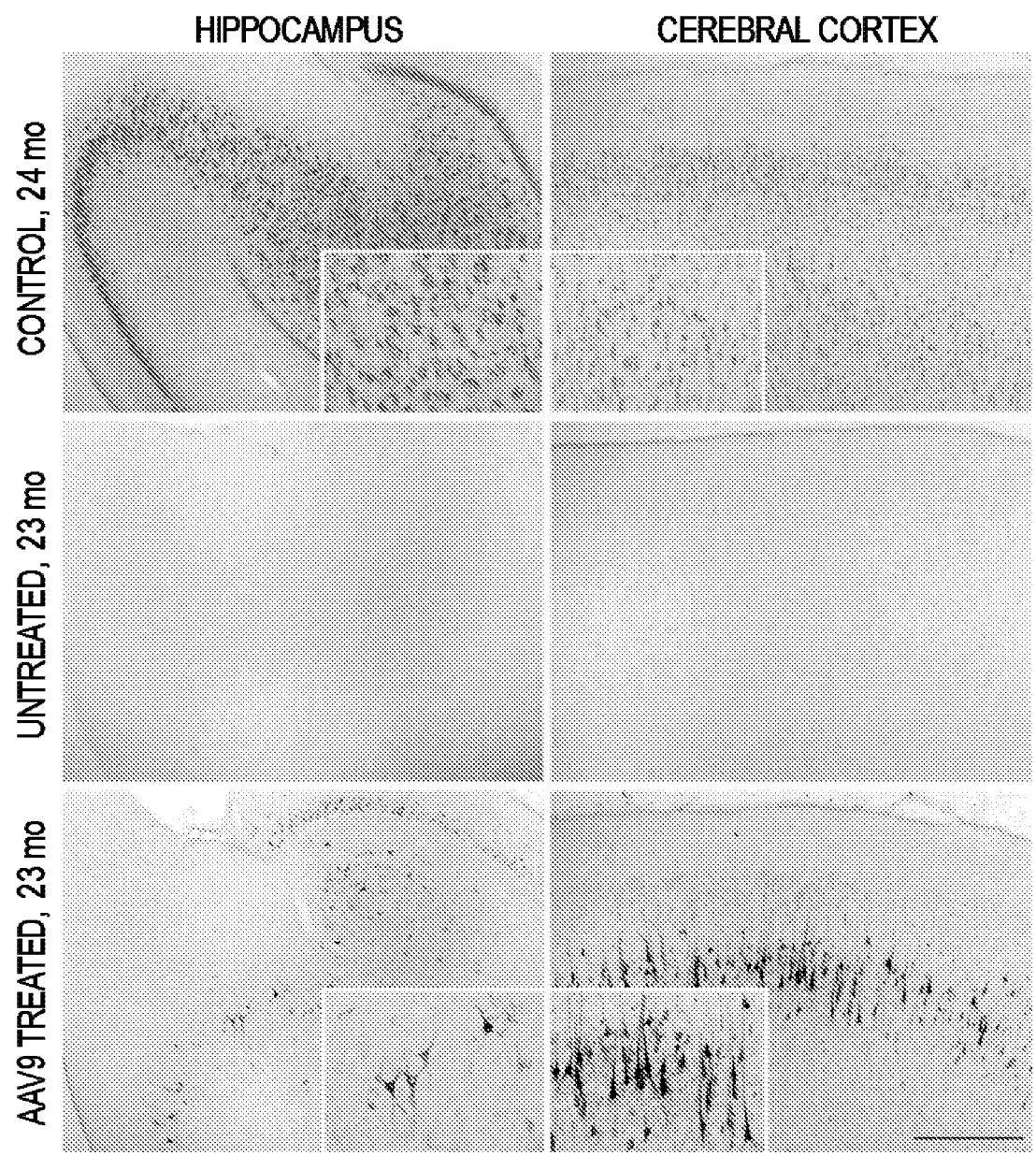
FIG. 7 shows long-term expression of the CLN5 protein after CLN5 gene therapy. Representative micrographs of the hippocampal and cortical regions in sagittal sheep brain sections of a CLN5$^{+/-}$ control, an untreated CLN5$^{-/-}$ sheep and a CLN5$^{-/-}$ sheep who received scAAV9-CLN5 treatment at 7 months, immunostained using an anti-rabbit CLN5 antibody. Endogenous CLN5 protein expression was evident throughout the control brain, which was lacking in the untreated CLN5$^{-/-}$ sheep brain. In contrast, strong CLN5 immunoreactivity was noted in the treated sheep brain over 15 months after intraventricular delivery of scAAV9.CLN5. CLN5-expressing cells in the treated hippocampal and cortical pyramidal cell layers were morphologically neuronal-like. Scale bar represents 500 µm.

Three scAAV9-treated animals were sacrificed at 23 months in order to determine the extent of CLN5 expression in the CNS. Immunohistochemistry revealed strong transduction throughout the brain, particularly in the hippocampus, cortical grey matter (FIG. 7) as well as the cerebellum and spinal cord.

Given that most human cases of NCL only become apparent on diagnosis following the development of disease symptoms, the second trial treated 7- and 9-month-old CLN5$^{-/-}$ sheep with established clinical disease. Self-complementary AAV vectors were used, following their purported 10- to 100-fold greater transduction efficiency than ssAAV9, which potentially reduces the doses required, increases efficacy and decreases the time between transduction and functional expression (McCarty et al., 2001 *Gene Ther.* 8: 1248-1254; Yang et al., 2002 *J. Virol.* 76: 7651-7660; Gray et al., 2011 *Mol. Ther.* 19: 1058-1069; Gray and Samulski 2011 *Gene Vector Design and Application to Treat Nervous System Disorders*, Society for Neuroscience: pp 1-9). The CBh promoter was chosen for its ability to provide strong, long-term, and ubiquitous CNS expression shown in other animal studies (Gray et al., 2011 *Hum. Gene Ther.* 22: 1143-1153).

The scAAV9 injections suspended disease progression in most of the 7-month treated sheep and one of the 9-month treated sheep. These animals remain alive today at 30-41 months. That they went blind at a similar rate to untreated CLN5$^{-/-}$ sheep was not unexpected as baseline intracranial volume measurements indicated considerable pre-injection atrophy of the occipital lobe, which continues in untreated CLN5$^{-/-}$ sheep (FIG. 5)(Amorim et al., 2015 *Brain Behav.* 5: e00401). Treatment halted this atrophy, little further occurring over the following 18-31 months (FIG. 4).

Simple maze tests based on those used in sheep for a number of applications, including spatial learning and memory studies, became a valuable adjunct to the clinical studies. Pre-clinically treated sheep retained their ability to navigate the maze well beyond the age at which untreated CLN5$^{-/-}$ sheep could not, at traverse times even faster than the unaffected cohort, possibly because they were more habituated to the food reward than the pasture-raised controls. Although they eventually went blind, differences on clinical examination and end-stage maze behaviour (e.g. hitting obstacles) suggest a difference in the pathophysiological cascade initiating visual disturbances from that in untreated CLN5$^{-/-}$ animals. Whereas loss of vision in the untreated CLN5$^{-/-}$ sheep paralleled atrophy of the visual cortex noted in histological, MRI and CT studies (FIGS. 3, 4 and 5), no such atrophy was observed in the pre-clinically treated brains, even at 27 months. It is likely that the gene therapy prevented the cortical neurodegenerative-driven blindness seen first in untreated CLN5$^{-/-}$ sheep but the vector and/or recombinant CLN5 protein did not penetrate to, or persist in, the retina to prevent its long-term degeneration. Thus the contemporaneous problems experienced by the treated sheep in navigating the maze were likely to be associated with the later onset retinal atrophy. This hypothesis is being explored in ongoing neuropathological examinations of the treated sheep brains which will also reveal any differences in efficacy and CLN5 biodistribution between the various promoters and doses used.

Similar findings were reported in dogs with CLN2 NCL after ICV AAV2-mediated delivery of the soluble lysosomal enzyme, tripeptidyl peptidase 1 (TPP1; Katz et al., 2015 *Sci. Transl. Med.* 7: 313ra180). Like the sheep, these dogs had an extended lifespan after treatment, with protection from cognitive decline and delayed disease onset and progression and a similar dichotomy of leading symptoms. Treatment did not delay the retinal degeneration in these dogs either.

The performance of certain animal species in cognitive or behavioural tasks, including maze tests, depends on visual ability. Here, GPS technology showed that although post-symptomatically treated sheep went blind and moved slowly, they could still navigate the maze at 22 months of age (FIG. 6) suggesting intact spatial memory skills learnt when still sighted. Untreated animals lose cognition and thus navigational ability well before this age. This technology will be important when testing the efficacy of future combined brain-directed and ocular gene therapies.

Sheep are ideal animals in which to assess the safety, efficacy and long-term prognosis of gene therapy. They share a large gyrencephalic brain and similar live body weights, spine dimensions, CSF volumes and pulmonary and cardiac parameters to humans. Presently sheep models of inherited disease are restricted to flocks arising from cases diagnosed on referral. Completion of the full genome sequence of sheep, and the advent of next generation sequencing technologies, make it feasible to screen populations of sheep for genetic variants to yield animal model candidates for an array of diseases. Recent advances in gene modification technologies, such as CRISPR/Cas9 genome editing, are being applied to sheep to generate purpose-built model flocks, thus increasing the use of this species for model studies. The in vivo tests described here will provide robust, quantitative natural history and translational data for these novel sheep models.

Treated sheep may eventually develop disease because of vector attenuation or the protein becoming non-functional with time. These considerations will determine the timing of the eventual post mortem neuropathology studies on the treated sheep still alive, and give an insight into whether medium term successful treatments could benefit from subsequent re-injections of vector, using serotypes chosen to prevent immune rejection. While intervention at the earliest possible stage will optimize patient outcome, CLN5 gene therapy to clinically affected animals still had a telling effect, slowing brain atrophy and delaying clinical progression indicating that clinically affected patients may also benefit.

Our studies so far indicate that ssAAV9, scAAV9 and LV vectors all resulted in effective transduction and amelioration of disease-related pathology. All of the viral cassettes contained the wild-type sheep CLN5 cDNA sequence, with translation from the ovine ATG initiation site in exon 1, which aligns with the third ATG in the human sequence, to yield a 361 amino acid peptide (Frugier et al., 2008 *Neurobiol. Dis.* 29: 306-315) in line with results of human lysosome proteomic studies (Sleat et al., 2009 *Mol. Cell Proteomics* 8: 1708-1708). Unfortunately a number of workers have assumed that the first ATG in the human CLN5 gene is the start codon leading to deductions from function and localization studies of uncertain veracity (Huber and Mathavarajah 2018 *Cell. Signal.* 42: 236-248; Jules et al., 2017 *Exp. Cell Res.* 357: 40-50). This must be borne in mind when designing vectors expressing the CLN5 protein for human treatments.

In conclusion these studies establish the efficacy of viral-mediated gene transfer in an ovine CLN5 NCL and provide a particularly pressing case for translation to patients, including those with clinically apparent disease, there being no other treatment options for patients bearing CLN5 mutations.

All references cited herein are incorporated herein by reference in their entireties and for all purposes to the same extent as if each individual publication or patent or patent application was specifically and individually indicated to be incorporated by reference in its entirety for all purposes.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A polynucleotide comprising a human neuronal ceroid lipofuscinosis protein 5 (CLN5) open reading frame, wherein the human CLN5 open reading frame is codon-optimized for expression in a human cell, wherein the codon-optimized human open reading frame starts from the third start site of the wildtype human CLN5, and wherein the human CLN5 open reading frame comprises the nucleotide sequence of SEQ ID NO:1 or a nucleotide sequence having at least 90% identity thereto.

2. An expression cassette comprising a polynucleotide comprising a human CLN5 open reading frame, wherein the polynucleotide is the polynucleotide of claim 1.

3. The expression cassette of claim 2, wherein the human CLN5 open reading frame is operably linked to a promoter, a polyadenylation signal, and/or an enhancer.

4. The expression cassette of claim 3, wherein the promoter is a chicken beta actin promoter, wherein the polyadenylation signal is a bovine growth hormone (BGH) polyadenylation signal, and/or wherein the enhancer is a cytomegalovirus (CMV) enhancer.

5. The expression cassette of claim 4, wherein the expression cassette comprises a first AAV2 ITR, a CMV enhancer, a chicken beta actin promoter, the human CLN5 open reading frame, a BGH polyadenylation site, and a second AAV2 ITR.

6. The expression cassette of claim 5, comprising the nucleotide sequence of SEQ ID NO:10 or a sequence at least about 90% identical thereto.

7. The expression cassette of claim 2, further comprising at least one adeno-associated virus (AAV) inverted terminal repeat (ITR).

8. The expression cassette of claim 2, wherein the expression cassette is a self-complementary AAV genome.

9. A viral vector comprising the polynucleotide of claim 1.

10. The viral vector of claim 2, wherein the vector is an AAV vector.

11. A transformed cell comprising the polynucleotide of claim 1.

12. A pharmaceutical composition comprising the polynucleotide of claim 1 in a pharmaceutically acceptable carrier.

* * * * *